(12) United States Patent
Rubin-Bejerano et al.

(10) Patent No.: US 8,617,823 B2
(45) Date of Patent: Dec. 31, 2013

(54) IMMUNOMODULATING COMPOSITIONS AND METHODS OF USE THEREOF

(75) Inventors: Ifat Rubin-Bejerano, Belmont, MA (US); Gerald R. Fink, Chesnut Hill, MA (US)

(73) Assignee: Immunexcite, Inc., Watertown, MA (US)

( * ) Notice: Subject to any disclaimer, the term of this patent is extended or adjusted under 35 U.S.C. 154(b) by 135 days.

(21) Appl. No.: 12/990,066

(22) PCT Filed: Apr. 29, 2009

(86) PCT No.: PCT/US2009/042117
§ 371 (c)(1),
(2), (4) Date: Apr. 12, 2011

(87) PCT Pub. No.: WO2009/134891
PCT Pub. Date: Nov. 5, 2009

(65) Prior Publication Data
US 2011/0177532 A1    Jul. 21, 2011

Related U.S. Application Data

(60) Provisional application No. 61/071,437, filed on Apr. 29, 2008.

(51) Int. Cl.
*G01N 33/53*    (2006.01)

(52) U.S. Cl.
USPC ............................................. 435/7.1; 435/7.2

(58) Field of Classification Search
None
See application file for complete search history.

(56) References Cited

U.S. PATENT DOCUMENTS

| | | |
|---|---|---|
| 5,480,642 A | 1/1996 | McCarthy |
| 2005/0208079 A1 | 9/2005 | Cassone et al. |
| 2006/0160766 A1 | 7/2006 | Cheung |
| 2006/0172353 A1 | 8/2006 | Mattsby-Baltzer et al. |
| 2011/0045049 A1* | 2/2011 | Rubin-Bejerano et al. ... 424/423 |

FOREIGN PATENT DOCUMENTS

| | | |
|---|---|---|
| WO | WO-2007/033315 A1 | 3/2007 |
| WO | WO-2008/057501 A2 | 5/2008 |

OTHER PUBLICATIONS

Tada et al. (Biosci Biotechnol. Biochem. 2009 vol. 73, p. 908-911).*
Bonaldo, Alessio, et al. "The influence of dietary beta-glucans on the adaptive and innate immune responses of European sea bass (*Dicentrarchus labrax*) vaccinated against vibriosis," Italian Journal of Animal Science, 6(2):151-164 (Apr. 2007).
Supplementary European Search Report for EP 09 73 9693 mailed Aug. 8, 2011.
Nishikawa, Y., et al.; "Polysaccharides in Lichens and Fungi. III. Further Investigation on the Structures and the Antitumor Activity of the Polysacchrides from *Gyrophora esculenta* Miyoshi and *Lasallia papulosa* Llano." Chem. Pharm. Bull. 17(9):1910-1916 (1969).
Rubin-Bejerano, I, et al.; "Phagocytosis by Human Neutrophils is Stimulated by a Unique Fungal Cell Wall Component," Cell Host Microbe. 2(1):55-67 (Jul. 12, 2007).
International Search Report for PCT/US2009/042117 dated Dec. 29, 2009.

* cited by examiner

*Primary Examiner* — Jacob Cheu

(74) *Attorney, Agent, or Firm* — Choate, Hall & Stewart, LLP

(57) ABSTRACT

The invention is directed to β1-6 glucans, compositions, diagnostic kits, and devices comprising the same, and methods of use thereof in modulating immune response and treating, delaying progression of, reducing the incidence or severity of cancer, infection, inflammation, and autoimmune diseases. The β1-6 glucans of certain embodiments of the invention are enriched for O-acetylated groups and/or conjugated to a solid support or linked to a targeting moiety. The β1-6 glucans of certain embodiments of the invention recruit immunoglobulin G antibodies to mediate complement and neutrophil killing. The conjugated β1-6 glucans of certain embodiments of the invention are targeted to cells to stimulate the immune response at the target location by activating complement-mediated lysis and recruitment of neutrophils.

38 Claims, 5 Drawing Sheets

A

B

IMMUNOMODULATING COMPOSITIONS AND METHODS OF USE THEREOF

RELATED APPLICATIONS

This application is a 371 National Stage Application of International Patent Application No. PCT/US2009/042117, filed on Apr. 29, 2009, which claims the benefit of priority to U.S. Provisional Patent Application Ser. No. 61/071,437, filed on Apr. 29, 2008; the entire contents of both applications are hereby incorporated by reference.

GOVERNMENT INTEREST STATEMENT

The invention was made in whole or in part with government support under Grant Number GM035010-22 awarded by the National Institute of Health. The government has certain rights in the invention.

BACKGROUND OF THE INVENTION

The cell walls of fungi evoke a powerful immuno-stimulatory response, and have been proposed for use as potential anti-infective and anti-tumor drugs. Fungal cells can also activate dendritic cells and prime class II restricted antigen specific T cell responses. The majority of the cell wall (50-60%) of pathogenic (*Candida albicans*) and non-pathogenic fungi (*Saccharomyces cerevisiae*) is composed of an inner layer of β-glucan (β-1,3- and β-1,6-glucan) covalently linked to a variety of cell surface mannoproteins [Klis, F. M. et al. Med Mycol 39 Suppl 1, 1-8, 2001; Klis, F. M. et al., FEMS Microbiol Rev 26, 239-56, 2002].

Recognition of β-glucans by macrophages is carried out mainly through Dectin-1 with cooperation of TLRs, including TLR2 [Brown, G. D. et al. Nature 413, 36-7, 2001]. Dectin-1 activity is inhibited by β-1,3-glucans and β-1,6-glucans, with the β-1,3-glucan laminarins having the highest effect. However, oligosaccharide microarray results show that Dectin-1 binds specifically to β-1,3-glucans. Neutrophils are professional killers, whose role in phagocytosis and killing of bacteria and fungi is well characterized. Neutropenic individuals are much more susceptible to bacterial and fungal infections, with return to normal counts playing an important role in resolution of infection. Neutrophils, unlike macrophages, require serum for optimal phagocytosis and killing. The main opsonic receptors are the complement receptor CR3 and the immunoglobulin-binding receptor FcγR. CR3 has a lectin domain [Brown, G. D. et al. *Immunity* 19, 311-5, 2003] that mediates increased neutrophil motility towards a mixture of β-1,3-glucan and β-1,6-glucan (PGG-glucan) [Wakshull, E. et al. *Immunopharmacology* 41, 89-107, 1999].

β-1,6-glucans have been found to provide potent anti-fungal activity, and inter alia, possess adjuvant activity and activate complement.

The complement (C) system of humans and other mammals involves more than 20 components that participate in an orderly sequence of reactions resulting in complement activation. Products derived from the activation of C components include non-self recognition molecules C3b, C4b and C5b, as well as the anaphylatoxins C3a, C4a and C5a that influence a variety of cellular immune responses (Hugh et al (1982) 15th International Leucocyte Culture Conference, Asilomar, C A (Abstract); Fujii et al. (1993) Protein Science 2:1301-1312; Morgan et al. (1982) J. Exp. Med. 155:1412-1426; Morgan (1993) Complement Today 1:56-75; Morgan et al. (1983) J. Immunol. 130:1257-1261). Complement activation occurs primarily via the "classical" pathway or the "alternative" pathway. The classical pathway is initiated by the binding of the first complement component (C1) to immune complexes through C1q, a subcomponent involved in binding to antibody. The c1 complex is composed of C1q and two homologous serine proteases, C1r and C1s (1:2:2 molar ratio). After binding to the immune complexes C1q undergoes a conformational change resulting in the conversions of C1r and C1s to their activated forms. Activated C1s cleaves C4 and C2 to generate a complex of their fragments C4b2a, which in turn cleaves C3 into C3a and C3b. C3b binds to immune complexes.

The alternative pathway is activated without involvement of antibody. C3b molecules generated from C3 by interaction of C3 with two serine proteases, factors B and D, are deposited on the microbial surface where activation of C3 is amplified. C3b produced by activation of either pathway acts as a central molecule in the subsequent formation of membrane attack complexes that can lyse microbes and also as an opsonin.

It is unknown whether β-1,6-glucans produce a robust immune response in all subjects and by what mechanism such response is generated.

SUMMARY OF THE INVENTION

This invention provides, in one embodiment, a diagnostic method for determining the responsiveness of a subject to a glucan-based vaccine or adjuvant, the method comprising:
assessing relative immunoglobulin G (IgG) 1, 2, 3 and 4 isotype titers in a subject exposed to a glucan; and
correlating the presence of high IgG1 or IgG2 or IgG3, or a combination thereof, versus IgG4 with responsiveness to a glucan-based vaccine or adjuvant.

In one embodiment, the method further comprises contacting a cell in the subject with a glucan-based vaccine or adjuvant prior to assessing relative IgG isotype titers, which in one embodiment comprises O-acetylated glucan, and in another embodiment, comprises glucan isolated or derived from a lichen or a fungus, wherein the fungus is optionally a yeast, which in one embodiment is isolated or derived from Umbilicariaceae. In another embodiment, the glucan-based vaccine or adjuvant comprises chemically synthesized or acetylated glucan, and in another embodiment, the glucan-based vaccine or adjuvant comprises glucan conjugated to a particle.

In one embodiment, the method further comprises administering a cytokine to said subject, which in one embodiment comprises interleukin 2, interleukin 12, interferon-γ, or a combination thereof.

In another embodiment, this invention provides a diagnostic kit for determining the responsiveness of a subject to a glucan-based vaccine or adjuvant, said kit comprising:
a glucan which corresponds to or is homologous to glucan in said vaccine or adjuvant;
reagents for detecting relative immunoglobulin G (IgG) 1, 2, 3 and 4 isotype titers in a subject sample; and
optionally a series of standards derived from positive and negative responders to said glucan-based vaccine or adjuvant.

According to this aspect of the invention, and in one embodiment, the glucan is attached to a substrate, which in one embodiment is a microtiter plate or in another embodiment is a bead. In one embodiment, the reagents comprise a detectable marker which renders the detection semi-quantitative.

In another embodiment this invention provides a method of stimulating an immune response in a subject, comprising administering to the subject purified β-1-6-glucan and an agent, which biases antibody production to yield relatively greater amounts of immunoglobulin G (IgG) 1, 2 or 3 versus immunoglobulin G (IgG) 4.

According to this aspect of the invention, and in one embodiment, the subject is administered the purified β-1-6-glucan and the agent concurrently, or in another embodiment the subject is administered purified β-1-6-glucan and the agent sequentially. In another embodiment the subject is administered said purified β-1-6-glucan and said cytokine each at least two times.

In one embodiment, the agent is a cytokine, which in one embodiment is interleukin-2, interleukin-12 or interferon-γ or a combination thereof. In another embodiment, the agent downmodulates interleukin-4 or interleukin-10 production or interferes with interleukin-4 or interleukin-10 activity.

In one embodiment, the subject is further exposed to an antigen associated with a target of the immune response, which in one embodiment is a tumor-associated antigen. According to this aspect of the invention, and in one embodiment, the subject has a hyperplastic or preneoplastic lesion, and in another embodiment, the method treats, delays progression of, prolongs remission of, or reduces the incidence or severity of cancer in the subject. In another embodiment, the subject has cancer. In another embodiment, the subject has not been diagnosed with cancer. In another embodiment, the subject has not been diagnosed with a tumor.

In another embodiment, the antigen is derived from a pathogen, which in one embodiment is a fungus. In one embodiment, the method treats, delays progression of, prolongs latency of, or reduces the incidence or severity of infection in the subject.

In one embodiment, the invention provides for use of a glucan-based vaccine or adjuvant, or a glucan, which comprises a particle comprising β1-6 glucan. In certain embodiments, the particle consists of at least 10%, 20%, 30%, 40%, 50%, 60%, 70%, 80%, 90%, 95%, 96%, 97%, 98%, or 99% β1-6 glucan by dry weight. In certain embodiments, the particle consists essentially of β1-6 glucan. Optionally, in certain embodiments, the β1-6 glucan is enriched for O-acetylated groups. The invention further provides methods and kits as described herein, which may make use of any of the aforementioned particles, or a composition containing any of the afore-mentioned particles.

In one embodiment, the β1-6 glucan is enriched for O-acetylated groups, which in one embodiment contains at least 25% by weight O-acetylated glucan.

In another embodiment, the glucan-based vaccines or adjuvants, or glucans for use according to this invention comprise β-1,3 glucans having β-1,6 glucan branches (also referred to as beta 1,3/1,6, glucan or beta-1,6-branched beta-1,3-glucan) wherein at least some of the β-1,6 glucan branches are enriched for O-acetylated groups. In another embodiment the invention makes use of a composition comprising (i) β1-6 glucan enriched for O-acetylated groups; and (ii) beta-1,6-branched beta-1,3-glucan.

In any embodiment of this invention, with regard to the term "contacting" or grammatical forms thereof, the contacting may occur either outside the body of a subject or within the body. In one embodiment, cells, which in some embodiments are neutrophils, are removed from a subject, contacted with the described agents or components or compositions, and then administered to the subject at a subsequent point in time. The cells (which, in some embodiments, are neutrophils or in other embodiments, other immune system cells, such as other professional antigen presenting cells, such as macrophages or dendritic cells, monocytes, NK cells, B cells or others) are contacted outside the body with an agent/component or composition of this invention and are then returned to the subject at which point another agent is administered to the subject, or another cell population is contacted outside the body with an agent/component or composition of this invention and are then returned to the subject. The suitable period of time could be, e.g., after the therapy has been administered and the desired results are not obtained, or for example, greater effects are desired, for example, immunoglobulin G4 (IgG4) production is too high, and following repeat administration of a cytokine, and subsequent exposure to the glucans, greater IgG1, 2 or 3 is produced.

In some embodiments, the invention provides kits which comprise a substrate comprising a glucan. In one embodiment, the substrate is a part of, or in the form of a microparticle, nanoparticle, microtiter plate, or any appropriate material for such diagnostic assays, for example, suitable for automated assay.

One aspect of the invention relates to a method for detecting the amount of immunoglobulin G (IgG) antibodies secreted in response to β-1,6-glucan; said method comprising the steps of:

obtaining a first blood sample from a subject prior to challenge with β-1,6-glucan;

obtaining a second blood sample from a subject after challenge with β-1,6-glucan; allowing a sufficient time to generate a signal readable in solution and detecting the signal in solution of IgG antibodies binding in an assay that quantifies or measures the presence of said IgG antibodies;

calculating said signal of IgG antibody binding from said first and second blood samples to determine the amount of IgG antibody secretion, wherein the difference between the signals indicate the amount of IgG antibodies produced in response to β-1,6-glucan; and comparing said difference to a positive and negative control; wherein said difference over a threshold determines the responsiveness of a subject to β-1,6-glucan.

In certain embodiments, said antibodies comprise whole immunoglobulin G or fragments thereof.

In certain embodiments, said antibodies may comprise isotypes selected from the group consisting of IgG1, IgG2, IgG3, and IgG4.

In certain embodiments, said antibodies are IgG2.

In certain embodiments, said subject may be human.

In certain embodiments, said β-1,6-glucan is isolated from a lichen, fungus, or yeast.

In certain embodiments, said β-1,6-glucan is isolated from Umbilicariaceae.

In certain embodiments, said β-1,6-glucan comprises O-acetylated β-1,6-glucan.

In certain embodiments, said β-1,6-glucan comprises chemically synthesized, genetically engineered, or O-acetylated β-1,6-glucan.

In certain embodiments, the amount of IgG antibodies is determine by enzyme-linked immunoassays, radioimmunoassays, immunoprecipitation, fluorescence immunoassays, chemiluminescent assay, immunoblot assays, lateral flow assays, agglutination assays, or particulate-based assays.

In certain embodiments, the pharmaceutical composition further comprises a β-1,6-glucan linked to a targeting moiety.

Another aspect of the invention relates to a diagnostic kit for measuring IgG levels, comprising:
(i) a pharmaceutical composition comprising β-1,6-glucan;
(ii) reagents for detecting IgG antibodies bound to said pharmaceutical composition in a blood sample;
(iii) optionally a series of standards derived from positive and negative responders to said pharmaceutical composition; and
(ii) instructions for using the pharmaceutical composition to detect IgG amounts in a blood sample.

In certain embodiments, said β-1,6-glucan is in solution or lyophilized

In certain embodiments, said β-1,6-glucan is immobilized on a substrate.

In certain embodiments, said substrate comprises a material selected from the group consisting of plastic, glass, gel, celluloid, paper, magnetic resin, polyvinylidene-fluoride, nylon, nitrocellulose, agarose, latex, and polystyrene.

In certain embodiments, said substrate comprises an ELISA plate, dipstick, microtiter plate, radioimmunoassay plate, beads, agarose beads, plastic beads, latex beads, immunoblot membranes, and immunoblot papers.

In certain embodiments, said reagent is conjugated to a detectable marker.

In certain embodiments, said detectable marker is selected from the group consisting of a radioactive label, fluorescent label, chemiluminescent label, chromophoric label, ligand, fluorescein, radioisotope, phosphatase, biotin, biotin-related compound, avidin, avidin-related compound, and peroxidase.

Another aspect of the invention relates to a composition comprising a β-1,6-glucan linked to a targeting moiety.

In certain embodiments, said glucan is O-acetylated.

In certain embodiments, said glucan contains at least 25% by weight O-acetylated glucan.

In certain embodiments, said glucan is isolated from a lichen, yeast, Fungus, chemically synthesized, or genetically engineered.

In certain embodiments, said glucan is isolated from Umbilicariaceae.

In certain embodiments, said targeting moiety is selected from the group consisting of an antibody, antigen, receptor ligand, epitope, polysaccharide, peptide, and any combination thereof.

In certain embodiments, said targeting moiety is an antigen; and the antigen is selected from the group consisting of a glycoprotein, mucoprotein, nucleic acid, carbohydrate, proteoglycan, lipid, mucin molecule, tumor-associated antigen, and any combination thereof.

In certain embodiments, said antigen is a tumor-associated antigen.

In certain embodiments, said tumor-associated antigen is present on a cancer cell selected from the group consisting of an ovarian carcinoma, melanoma, pancreatic carcinoma, colorectal carcinoma, Burkitt's lymphoma, B-cell lymphoma, lung carcinoma, leukemia, breast carcinoma, myeloid carcinoma, colonic adenocarcinoma, gastric carcinoma, embryonal carcinoma, prostate carcinoma, and endometrial carcinoma.

In certain embodiments, said cancer cell is an ovarian carcinoma; and said tumor-associated antigen is a CA125 or CD46.

In certain embodiments, said cancer cell is a melanoma cell; and said tumor-associated antigen is selected from the group consisting of a p97, gp75, HMW-MAA, ganglioside GD2, ganglioside GD3, MAGE, BAGE, Mart-1R24, ganglioside GM2, and ganglioside GM3.

In certain embodiments, said cancer cell is a pancreatic carcinoma; and said tumor-associated antigen present is an ADMR or CRLR.

In certain embodiments, said cancer cell is a carcinoembryonic carcinoma; and said tumor-associated antigen is a CEA.

In certain embodiments, said cancer cell is a colorectal carcinoma; and said tumor-associated antigen is selected from the group consisting of a TAG-72, CO17-1A, GICA 19-9, CTA-1, LEA, VEP8, VEP9, Myl, VIM-D5, D156-22, C4BP, and DAF.

In certain embodiments, said cancer cell is a Burkitt's lymphoma; and said tumor-associated antigen is an antigen-38.13 or CD19.

In certain embodiments, said cancer cell is a human B-lymphoma; and said tumor-associated antigen is a CD20 or CD33.

In certain embodiments, said cancer cell is a human lung carcinoma; and said tumor-associated antigen is a L6, L20, F3, or CD117.

In certain embodiments, said cancer cell is a human leukemia T cell; and said tumor-associated antigen is a gp37, neoglycoprotein, sphingolipids, or APO-1.

In certain embodiments, said cancer cell is a breast carcinoma cell; and said tumor-associated antigen is an EGFR, HER/neu, CR1, M18, or M39.

In certain embodiments, said cancer cell is a myeloid carcinoma; and said tumor-associated antigen is a T5A7 or SSEA-1.

In certain embodiments, said cancer cell is a colonic adenocarcinoma cell; and said tumor-associated antigen is a C14, CO-514, or NS-10.

In certain embodiments, said cancer cell is a gastric carcinoma cell; and said tumor-associated antigen is a mucin, AH6, or FHL-1.

In certain embodiments, said cancer cell is an embryonal carcinoma cell; and said tumor-associated antigen is selected from the group consisting of a Y hapten, Ley, FC10.2, 4.2, GD3, D1.1, OFA-1, GM2, OFA-2, GD2, and M1:22:25:8.

In certain embodiments, said cancer cell is a prostate carcinoma; and said tumor-associated antigen is a CD55 or MCP.

In certain embodiments, said cancer cell is an endometrial carcinoma; and said tumor-associated antigen is a CD35.

In certain embodiments, said targeting moiety is an epitope; and said epitope is selected from the group consisting of a T helper cell epitope (TH), chemokine epitope, neutrophilic epitope, MHC class II molecule, and phagocytic epitope.

In certain embodiments, said epitope is a neutrophilic epitope; and said neutrophilic epitope is selected from the group consisting of a L-selectin, 2-integrins, complement receptor 1 (CR-1), decay-accelerating factor (DAF), C5a receptor, intercellular adhesion molecule-1 (ICAM-1), and ICAM-3.

In certain embodiments, said epitope is a phagocytic epitope; and said phagocytic epitope is a Fc receptor.

In certain embodiments, said epitope is a chemokine epitope; and said chemokine epitope is a CD40, CD80, or CD86.

In certain embodiments, said epitope is a MHC class II molecule; and said MHC class II molecule is selected from the group consisting of a CD69, ADAMS, CD14, CD163, CD33, CD63, CD68, CD74, CHIT1, CHST10, CSF1R, DPP4, FABP4, FCGR1A, ICAM2, IL1R2, ITGA1, ITGA2, S100A8, and TNFRSF8.

In certain embodiments, said TH epitope is capable of being taken up by an antigen presenting cell (APC) which is capable of being processed by the APC whereby the APC presents the TH epitope on its surface bound to an MHC class II molecule.

In certain embodiments, said targeting moiety is an antibody; and said antibody is selected from the group consisting of a monoclonal antibody, polyclonal antibody, bispecific antibody, diabody, tribody, tetrabody, and minibody.

In certain embodiments, said antibody is a monoclonal antibody.

In certain embodiments, said monoclonal antibody is selected from the group consisting of an Alemtuzumab (Campath), Bevacizumab (Avastin), Cetuximab (Erbitux), Gemtuzumab (Mylotarg), Ibritumomab (Zevalin), Panitumumab (Vectibix), Rituximab (Rituxan), Tositumomab (Bexxar), Trastuzumab (Herceptin), Palivizumab (Synagis) in A and F protein in respiratory syncytial virus, and Immunoglobulin G2.

In certain embodiments, said monoclonal antibody is Alemtuzumab (Campath); and said Alemtuzumab (Campath) targets CD52 present on pancreatic carcinoma cells.

In certain embodiments, said monoclonal antibody is Bevacizumab (Avastin); and said Bevacizumab (Avastin) targets VEGF present in colorectal carcinomas.

In certain embodiments, said monoclonal antibody is Cetuximab (Erbitux); and said Cetuximab (Erbitux) targets EGFR present on head neck squamous cell carcinomas or breast carcinomas.

In certain embodiments, said monoclonal antibody is Gemtuzumab (Mylotarg); and said Gemtuzumab (Mylotarg) targets CD33 present on myeloid leukemias.

In certain embodiments, said monoclonal antibody is Ibritumomab (Zevalin), Panitumumab (Vectibix), Rituximab (Rituxan), or Tositumomab (Bexxar); and said Ibritumomab (Zevalin), Panitumumab (Vectibix), Rituximab (Rituxan), or Tositumomab (Bexxar) targets CD20 present on B-cell lymphomas.

In certain embodiments, said monoclonal antibody is Trastuzumab (Herceptin); and said Trastuzumab (Herceptin) targets HER/neu present on breast carcinomas.

In certain embodiments, said monoclonal antibody is Palivizumab (Synagis); and said Palivizumab (Synagis) targets A and F protein present on respiratory syncytial viruses.

In certain embodiments, said monoclonal antibody is immunoglobulin G; and said immunoglobin G targets β-1,6-glucan present on fungal or bacterial pathogens.

In certain embodiments, said antibody is a polyclonal antibody; and said polyclonal binds to any of the aforementioned antigens or epitopes.

In certain embodiments, said antibody comprises at least one antigen-binding site that binds to IgG2.

In certain embodiments, said antibody comprises a second, third or fourth antigen-binding site to any of the aforementioned antigens and epitopes.

In certain embodiments, the composition further comprises administering concurrently or successively an adjuvant, an antigen, an immunomodulatory compound, or a combination thereof.

Another aspect of the invention relates to a pharmaceutical formulation, comprising a composition of any of the aforementioned compostions of β-1,6-glucan linked to a targeting moiety; and a pharmaceutically acceptable carrier, diluent, or excipient.

Another aspect of the invention relates to a method for modulating an immune response in a subject, comprising administering to a subject in need thereof a therapeutically effective amount of a composition of any of the aforementioned compositions of β-1,6-glucan linked to a targeting moiety.

In certain embodiments, said immune response to a target cancer cell, infectious agent, pathogen, or site of infection is stimulated.

In certain embodiments, said immune response stimulates or enhances heat shock protein expression.

In certain embodiments, said immune response induces the production of reactive oxygen species (ROS).

In certain embodiments, said immune response enhances or stimulates neutrophilic phagocytosis or cytotoxic lysis.

In certain embodiments, said immune response enhances or stimulates complement-mediated lysis.

In certain embodiments, the method further comprises administering concurrently or successively an adjuvant, an antigen, a peptide, an immuno-stimulatory compound, a therapeutic agent, or a combination thereof.

In certain embodiments, said therapeutic agent is selected from the group consisting of an anti-inflammatory, antiviral, antibiotic, anti-infective, glucan synthesis inhibitors, antiprotozoal, antihistamine, decongestant, antipsychotics, mitotic inhibitor, and any combination thereof.

In certain embodiments, said therapeutic agent is an antiviral; and said antiviral is acyclovir, nelfinavir, or virazole.

In certain embodiments, said therapeutic agent is an antibiotic; and said antibiotic is selected from a group consisting of ampicillin, penicillin G, penicillins, cephalosporins, aminoglycosidics, macrolides, carbapenem, penem, beta-lactam monocyclic, inhibitors of beta-lactamases, tetracycline, polipeptidic antibiotics, chloramphenicol, fusidic acid, lincomicyn, novobiocine, spectinomycin, poly-etheric ionophores, and quinolones.

In certain embodiments, said therapeutic agent is an anti-infective; and said anti-infective is selected from the group consisting of benzalkonium chloride, chlorhexidine; dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin, ticarcillin, rifampin, tetracycline, diflunisal, ibuprofen, indomethacin, meclofenamate, mefenamic acid, naproxen, oxyphenbutazone, phenylbutazone, piroxicam, sulindac, tolmetin, aspirin, salicylates, and amphotericin B.

In certain embodiments, said therapeutic agent is a glucan synthesis inhibitor; and said glucan synthesis inhibitor is selected from the group consisting of caspofungin, micafungin, anidulafungin (LY303366), econazole, terconazole, fluconazole, voriconazole, and griseofulvin.

In certain embodiments, said therapeutic agent is an antiprotozoal; and said antiprotozoal is a metronidazole, tubulazole, thiabendazole, or oxfendazole.

In certain embodiments, said therapeutic agent is an antihistamine; and said antihistamine is astemizole, levocabastine, cetirizine, or cinnarizine.

In certain embodiments, said therapeutic agent is a decongestant; and said decongestant is pseudoephedrine.

In certain embodiments, said therapeutic agent is an antipsychotic; and said antipsychotic is fluspirilene, penfluridole, risperidone, or ziprasidone.

In certain embodiments, said therapeutic agent is an mitotic inhibitor; and said mitotic inhibitor is etoposide, colchicine, or vinca alkaloids.

In certain embodiments, said immune response is downregulated or abrogated.

In certain embodiments, said immune response downregulates or abrogates activation of interferon, interleukin, tumor necrosis factor, granulocyte-macrophage colony stimulating factor (GM-CSF), macrophage colony stimulating factor (M-CSF), granulocyte colony stimulating factor (G-CSF), neutrophil activating protein (NAP), macrophage chemoattractant and activating factor (MCAF), RANTES, or macrophage inflammatory peptides.

In certain embodiments, the method further comprises administering concurrently or successively an immunosuppressant.

Another aspect of the invention relates to a method of treating, delaying progression of, prolonging remission of, or reducing the incidence or severity of cancer in a subject, comprising administering to a subject in need thereof a therapeutically effective amount of a composition of any of the aforementioned compositions of β-1,6-glucan linked to a targeting moiety.

In certain embodiments, said immune response to a target cancer cell, a hyperplastic lesion, or a preneoplastic lesion is stimulated.

In certain embodiments, said immune response enhances neutrophilic phagocytosis, stimulates cytotoxic lysis, induces production of ROS, induces the expression of heat shock proteins, or enhances complement-mediated lysis.

In certain embodiments, the method further comprises administering concurrently or successively a chemotherapeutic agent, a cytotoxic agent, an anti-neoplastic agent, or a combination thereof.

In certain embodiments, said cytotoxic agent is selected from the group consisting of an ErbB receptor inhibitor, VEGF receptor inhibitor, tyrosine kinase inhibitor, protein kinase A inhibitor, anti-angiogenic agent, anti-hormonal agent, and cytokine.

In certain embodiments, said chemotherapeutic agent is selected from the group consisting of a cisplatin, doxorubicin, gemcitabine, docetaxel, paclitexel, and belomycin.

In certain embodiments, said antineoplastic agent is selected from the group consisting of spiroplatin, cisplatin, carboplatin, methotrexate, fluorouracil, adriamycin, mitomycin, ansamitocin, bleomycin, cytosine arabinoside, arabinosyl adenine, mercaptopolylysine, vincristine, busulfan, chlorambucil, melphalan, PAM, L-PAM, phenylalanine mustard, mercaptopurine, mitotane, procarbazine hydrochloride actinomycin D, daunorubicin hydrochloride, doxorubicin hydrochloride, paclitaxel and other taxenes, rapamycin, manumycin A, TNP-470, plicamycin, mithramycin, aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea, procarbazine, and dacarbazine.

In certain embodiments, the method further comprises administering concurrently or successively an adjuvant, an antigen, an immuno-modulatory compound, or a combination thereof.

Another aspect of the invention relates to a method of treating, delaying progression of, or reducing the incidence or severity of an infection in a subject, comprising administering to a subject in need thereof a therapeutically effective amount of any of the aforemention compositions of β-1,6-glucan linked to a targeting moiety.

In certain embodiments, said immune response to a target parasite, virus, fungus, pathogen, bacteria, or infectious agent is stimulated.

In certain embodiments, said immune response enhances neutrophilic phagocytosis, stimulates cytotoxic lysis, induces production of ROS, induces the expression of heat shock proteins, or enhances complement-mediated lysis.

In certain embodiments, the method further comprises administering concurrently or successively an antibiotic, an antiviral, an anti-infective, an antiprotozoal, an adjuvant, an antigen, an immuno-modulatory compound, or a combination thereof.

Another aspect of the invention relates to a method of treating, delaying progression of, reducing the incidence or severity of inflammation in a subject, comprising administering to a subject in need thereof a therapeutically effective amount of any of the aforementioned compositions of β-1,6-glucan linked to a targeting moiety.

In certain embodiments, said inflammation at a target inflammatory foci is downregulated or abrogated.

In certain embodiments, the method further comprises administering concurrently or successively an adjuvant, an antigen, a peptide, an immuno-stimulatory compound, an anti-inflammatory agent, or a combination thereof.

In certain embodiments, said anti-inflammatory agent is selected from the group consisting of betamethasone, prednisolone, piroxicam, aspirin, flurbiprofen, and (+)-N-{4-[3-(4-fluorophenoxy)phenoxy]-2-cyclopenten-1-yl}-N-hyroxyurea.

Another aspect of the invention relates to a method of treating, delaying progression of, or reducing the incidence or severity of an autoimmune response in a subject, comprising administering to a subject in need thereof a therapeutically effective amount of any of the aforementioned compositions of β-1,6-glucan linked to a targeting moiety.

In certain embodiments, said autoimmune response to a target transplanted tissue, transplanted cells, autoantigen, or HIV infection is downregulated or abrogated.

In certain embodiments, said autoimmune response downregulates activation of interleukin, tumor necrosis factor, or interferon.

In certain embodiments, the method further comprises administering concurrently or successively an immunosuppressant.

Another aspect of the invention relates to a composition comprising purified β-1,6-glucan linked to a targeting moiety, wherein the composition is a pharmaceutical composition, a food or food product, a food supplement, or a cosmetic composition.

In certain embodiments, the composition comprises β-1,6-glucan linked to a targeting moiety that has been processed to increase its ability to modulate the immune response relative to unprocessed β-1,6-glucan.

In certain embodiments, at least 95% of the glucan contained in the composition is β-1,6-glucan linked to a targeting moiety.

Another aspect of the invention relates to a micelle comprising β-1,6-glucan linked to a targeting moiety, wherein said β-1,6-glucan is optionally O— acetylated.

Another aspect of the invention relates to a composition comprising β-1,6-glucan linked to a targeting moiety and a biodegradable polymer, wherein said biodegradable polymer degrades to form biologically active salicylate or alpha-hydroxy acid moieties and said β-1,6-glucan is optionally O-acetylated.

Another aspect of the invention relates to a particle comprising a microsphere linked to any of the aforementioned compositions of β-1,6-glucan linked to a targeting moiety and a biodegradable polymer.

Another aspect of the invention relates to a medical device comprising the composition of any of the aforementioned compositions of β-1,6-glucan linked to a targeting moiety and a biodegradable polymer.

In certain embodiments, at least a portion of a surface is coated with a composition comprising a β-1,6-glucan linked to a targeting moiety.

In certain embodiments, the device is selected from the group consisting of a catheter, stent, valve, pacemaker, central line, pessary, tube, shunt, feeding tube, drain, and orthopedic hardware devices.

In certain embodiments, the composition comprises a coating layer comprising a polymer and β-1,6-glucan linked to a targeting moiety.

In certain embodiments, the composition comprises a coating layer comprising a polymer and β-1,6-glucan linked to a targeting moiety, wherein the polymer is biodegradable.

Another aspect of the invention relates to a method of treating a subject comprising implanting or introducing any of the aforementioned medical devices into the body of a subject in need thereof.

Another aspect of the invention relates to a coated material comprising: (a) a substrate; and (b) a composition comprising a β-1,6-glucan linked to a targeting moiety that is physically associated with at least a portion of a surface of said substrate, wherein said composition is optionally in the form of a gel or film.

In certain embodiments, the composition is a polymer.

In certain embodiments, the composition comprises a biodegradable polymer.

In certain embodiments, the substrate is composed at least in part of metal, ceramic, or polymer.

Another aspect of the invention relates to a method of treating a subject comprising contacting the body of a subject in need thereof with the coated material of any of the aforementioned coated materials.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or subrange within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

Figure 1:
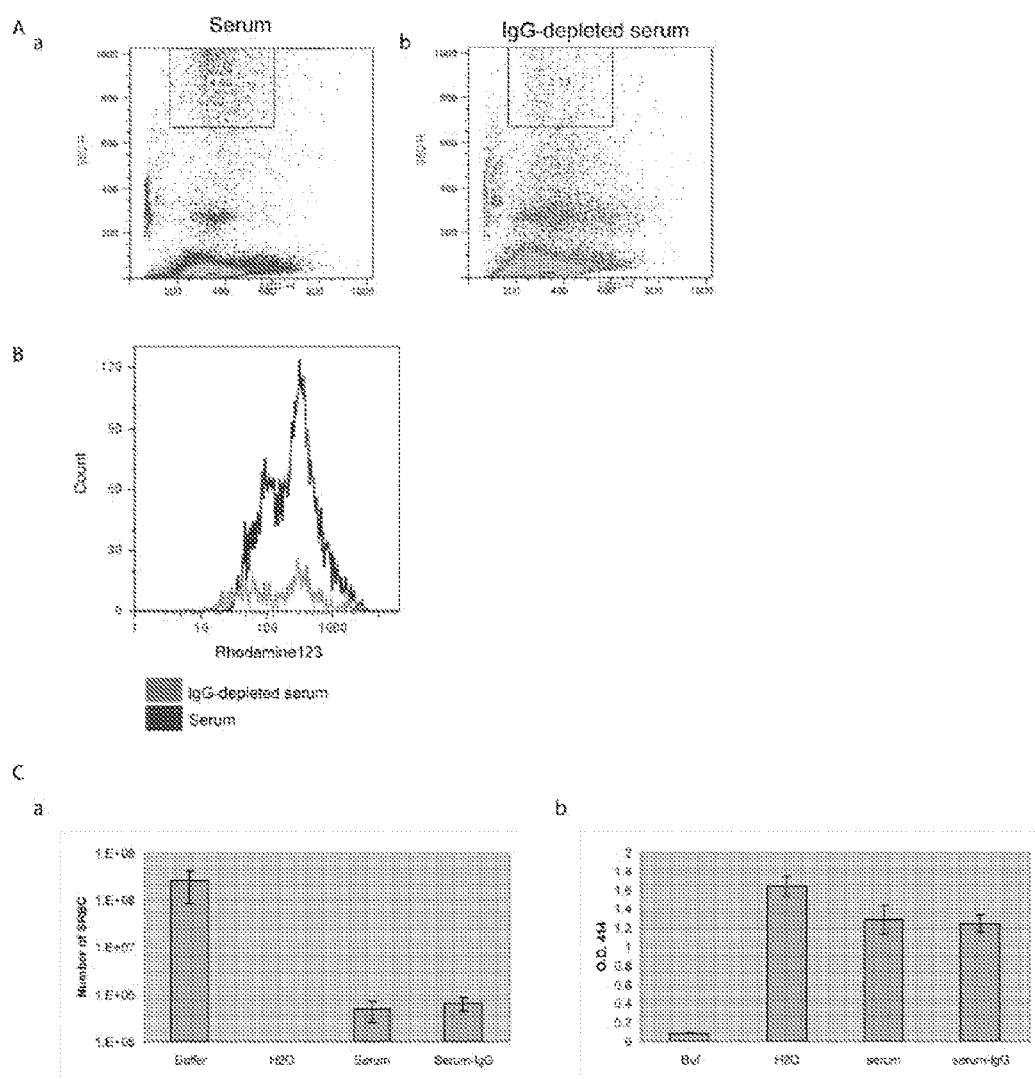
FIG. 1 demonstrates engulfment of β-1,6-glucan-coated beads (A) and ROS production (B) are antibody dependent, irrespective of the presence of complement (C).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Glucans are polysaccharides found so far in all studied species of lichenized fungi. Partially O-acetylated pustulans are typical of Umbilicariaceae, and have been described for several species of *Umbilicaria*, such as *U. pustulata* and *U. hirsute, U. angulata, U. caroliniana,* and *U. polyphylla*.

Responsiveness to β-1,6-glucans, were found by the inventors to be antibody-dependent, and robustness of this response was found to be associated with subjects having particular immunoglobulin G (IgG) isotype expression. Such expression may be useful therefore in predicting a subject's responsiveness to glucan-based vaccines or adjuvants, and such activity may be useful in modulating immune responses.

In one embodiment, the invention provides a diagnostic method for determining the responsiveness of a subject to a glucan-based vaccine or adjuvant, the method comprising:
assessing relative immunoglobulin G (IgG) 1, 2, 3 and 4 isotype titers in a subject exposed to a glucan; and
correlating the presence of high IgG1 or IgG2 or IgG3, or a combination thereof, versus IgG4 with responsiveness to a glucan-based vaccine or adjuvant.

In some embodiments, such method may be practiced on any biological fluid of or sample isolated from the subject. In some embodiments, such method is practiced on serum or plasma isolated from a subject It is to be appreciated that there are many methods known in the art for assessing IgG isotype titers, for example, a modified ELISA assay may be conducted, where a glucan or a fragment thereof is adsorbed to a substrate, which is then incubated with the fluid or sample from the subject, such that glucan-induced antibody isotype may be determined by probing with enzyme-labeled anti-IgG subclass-specific secondary antibody. Other assays, such as the Ouchterlony (double diffusion) assay, or other single-step identification methods, which are commercially available, may be utilized, as well.

In one embodiment, the method specifically assesses relative differences in IgG isotype expression in a given sample, such that the relative increase in IgG1, IgG2 or IgG3 versus that of IgG4 serves as an indicator for responsiveness to the glucan-based vaccine or adjuvant.

In one embodiment, the method further comprises contacting a cell in the subject with a glucan-based vaccine or adjuvant prior to assessing relative IgG isotype titers, which in one embodiment comprises O-acetylated glucan, and in another embodiment, comprises glucan isolated or derived from a lichen or a fungus, wherein the fungus is optionally a yeast, which in one embodiment is isolated or derived from Umbilicariaceae.

In some embodiments, the methods of this invention make use of a composition comprising purified β1-6 glucan, wherein the composition is, in various embodiments of the invention, a pharmaceutical composition, a food or food product, a food supplement, or a cosmetic composition. The composition is, in some embodiments, distinct from compositions such as pustulan or preparations of fungal cell walls. In certain embodiments of the invention at least 10%, 20%, 30%, 40%, 50%, 60%, 70%, 80%, 90%, 95%, 98%, or 99% of the glucan contained in the composition by weight is β1-6 glucan. In certain embodiments between 20% and 50% of the glucan contained in the composition is β1-6 glucan. In certain embodiments between 50% and 100% of the glucan contained in the composition is β1-6 glucan. In one embodiment of any of the compositions or methods of the invention, the glucan contains from about 15% to about 30% by weight β1-6 glucan. In another embodiment of any of the compositions or methods of the invention, the glucan contains from about 10% to about 35% by weight β1-6 glucan, or in another embodiment, from about 20% to about 50% by weight β1-6 glucan, or in another embodiment, from about 25% to about 60% by weight β1-6 glucan, or in another embodiment, from about 35% to about 80% by weight β1-6 glucan, or in another embodiment, from about 18% to about 35% by weight β1-6 glucan, or in another embodiment, from about 15% to about 75% by weight β1-6 glucan. In certain embodiments, said glucan is a mixture of oligomers or polymers, wherein the β-1,6-glucan is greater than about 10%, 20%, 30%, 40%, 50%, 60%, 70%, 80%, 90%, 95%, 98%, or 99% by weight of those oligomers or polymers. In certain embodiments of the invention "weight" refers to "dry weight". In other embodiments "weight" refers to total weight. In certain embodiments of the invention the β1-6 glucan is processed. Such processing may comprise, for example, deacetylation, treatment with enzymes that digest glucans other than β1-6 glucan, limited digestion with enzymes that digest β1-6 glucan, selection of particular molecular weight ranges, etc. In certain embodiments, processing comprises separation from other glucans, e.g., α-glucans, β-3 glucans, etc. In certain embodiments the processing comprises removing β-6 glucan side chains from β-3 glucans and optionally separating the β1-6 glucans side chains. In certain embodiments the composition comprises processed β1-6 glucan, wherein the processed β1-6 glucan exhibits enhanced ability to desirably modulate the immune response relative to unprocessed glucan or relative to unprocessed β1-6 glucan.

This invention makes use, in one embodiment, of β1-6 glucan enriched for O-acetylated groups. In one embodiment, in any of the preparations for use according to the methods of the invention, the glucan contains at least 25% by weight O-acetylated glucan. In one embodiment, in any of the preparations for use according to the methods of the invention, the glucan contains from about 15% to about 30% by weight O-acetylated glucan. In another embodiment, in any of the preparations for use according to the methods of the invention, the glucan contains from about 10% to about 35% by weight O-acetylated glucan, or in another embodiment, from about 20% to about 50% by weight O-acetylated glucan, or in another embodiment, from about 25% to about 60% by weight O-acetylated glucan, or in another embodiment, from about 35% to about 80% by weight O-acetylated glucan, or in another embodiment, from about 18% to about 35% by weight O-acetylated glucan, or in another embodiment, from about 15% to about 75% by weight O-acetylated glucan. In other embodiments, the glucan contains between about 75% and 100% by weight O-acetylated glucan, e.g., between 75% and 90%, or between 90% and 100% by weight O-acetylated glucan. In one embodiment, in any of the preparations for use according to the methods of the invention, the glucan contains approximately that percentage of O-acetylated glucose units (by weight or number, in various embodiments of the invention) that would result from digestion of a naturally occurring β1-6 glucan (e.g., pustulan or any other β1-6 glucan mentioned herein) with a β1-6 endoglucanase for a time sufficient to digest at least 90% by weight of the β1-6 glucan to oligosaccharides comprising 5 or fewer glucose units followed by (i) removal of those oligosaccharides comprising 5 or fewer glucose residues from the composition or (ii) isolation of a portion of the resulting composition having a molecular weight greater than 5 kD, or in some embodiment greater than 10, 20, 30, 50, or 100 kD.

In some embodiments, the term "enriched for O-acetylated residues" refers to the enhanced % of O-acetylated sites in individual glucose units within the glucan molecule, enhanced % of O-acetylated glucose units within the glucan molecule, or a combination thereof, as compared to a native glucan molecule. In one embodiment, reference to glucan preparations enriched by a particular weight percent for O-acetylated glucan, refers to preparations comprising an enhanced % of O-acetylated sites in individual glucose units within the glucan molecule, an enhanced % of O-acetylated glucose units within the glucan molecule, or a combination thereof, as compared to a glucan molecule.

Glucans derived from different sources may comprise varying amounts of O-acetylation in terms of O-acetylated sites in individual glucose units, O-acetylated glucose units within the glucan molecule, or a combination thereof. According to this aspect of the invention, the term "enriched for O-acetylated glucan" refers, in some embodiments, to enhanced O-acetylation as described herein, between the reference source from which the glucan is derived, and may not represent an overall enrichment as compared to any glucan source.

In one embodiment, the term "enriched for O-acetylated glucan" refers, to an enrichment of at least 25% by weight of the glucan chains, which are O-acetylated on at least one glucose unit, or at least 25% of the glucose units present in the glucan in the composition are O-acetylated, or a combination thereof. In some embodiments, at least 25% of the glucose units in at least 1%, or in another embodiment, at least 5% of the beta glucan chains are O-acetylated. In other embodiments between 25% and 35%, between 25% and 50%, between 25% and 75%, between 15% and 45%, between 20% and 60%, between 35% and 80%, or others of the glucose units in at least 5% of the beta glucan chains are O-acetylated, etc. In other embodiments, embodiments between 25% and 35%, between 25% and 50%, between 25% and 75%, between 15% and 45%, between 20% and 60%, between 35% and 80%, or others of the glucose units, in at least 10% of the beta glucan chains, or in another embodiment, in at least 15% of the beta glucan chains, or in another embodiment, in at least 20% of the beta glucan chains, are O-acetylated.

In one embodiment, the glucan is isolated or derived from a lichen, which in one embodiment is from the genus Umbilicariaceae. In one embodiment, the glucan is isolated from a fungus. In one embodiment, the glucan is isolated from yeast, or in another embodiment the glucan is chemically synthesized or acetylated. In another embodiment, the glucan is conjugated to a solid support.

Glucans are glucose-containing polysaccharides found inter alia in fungal cell walls. α-glucans include one or more α-linkages between glucose subunits and β-glucans include one or more β-linkages between glucose subunits β-1,6-glucans occur frequently in fungi but are rarer outside fungi. The glucan used in accordance with the invention comprises β1,6 glucan. In some embodiments, the β-glucans are derived from Umbilicariaceae, such as *U. pustulata* and *U. hirsute, U. angulata, U. caroliniana*, and *U. polyphylla*.

In some embodiments, the β-glucans are derived from *Candida*, such as *C. albicans*. Other organisms from which β-glucans may be used include *Coccidioides immitis, Trichophyton verrucosum, Blastomyces dermatidis, Cryptococcus neoformans, Histoplasma capsulatum, Saccharomyces cerevisiae, Paracoccidioides brasiliensis*, and *Pythiumn insidiosum*. In some embodiments, the β-glucans are chemically or enzymatically synthesized, as is known in the art, or in other embodiments, the β-glucans are derived from any species producing the same, and chemically or enzymatically altered, for example, to increase O-acetylation of the molecule.

In some embodiments, the β-glucans are fungal glucans. A 'fungal' glucan will generally be obtained from a fungus but, where a particular glucan structure is found in both fungi and non-fungi (e.g., in bacteria, lower plants or algae) then the non-fungal organism may be used as an alternative source.

Full-length native β-glucans are insoluble and have a molecular weight in the megadalton range. In some embodiments, this invention provides soluble β-1,6-glucan. In some embodiments, this invention provides soluble O-acetylated β-1,6-glucan. Solubilization may be achieved by fragmenting long insoluble glucans, in some embodiments. This may be achieved by, for example, hydrolysis or, in some embodiments, by digestion with a glucanase (e.g., with a β-1,3 glucanase or limited digestion with a β-1,3 glucanase). In other embodiments, glucans can be prepared synthetically, for example, and in some embodiments, by joining monosaccharide building blocks. O-acetylation of such glucans can readily be accomplished by methods known in the art. Such methods may include chemical and/or enzymatic acetylation, such as are known in the art.

There are various sources of fungal β-glucans. For instance, pure β-glucans are commercially available e.g., pustulan (Calbiochem) is a β-1,6-glucan purified from *Umbilicaria papullosa*. β-glucans can be purified from fungal cell walls in various ways, for example, as described in Tokunaka et al. [(1999) Carbohydr Res 316:161-172], and the product may be enriched for β-1,6-glucan moieties, or O-acetylated β-1,6-glucan moieties, by methods as are known in the art.

One of ordinary skill in the art will be able to identify or select appropriate methods to enrich for β-1,6-glucan moieties and/or for O-acetylated β-1,6-glucan. In one embodiment, O-acetylation of beta-glucan is performed chemically. For example, polysaccharides (50 mg) are dried in a speed vac centrifuge and resuspended in 1.5 mL of acetic anhydride (Mallindcrockdt). After resuspension, a few crystals of 4-dimethylaminopyridine (Avocado Research Chemist, Ltd) are added as catalyst. The reaction is allowed to proceed at room temperature for 5, 20, or 120 minutes and then stopped with 2 volumes of water. Afterwards the samples are dialyzed overnight against water. It will be appreciated that this process could be varied or scaled up, as evident to one of skill in the art. In other embodiments, methods for separating O-acetylated β-1,6-glucan include one or more of the following steps, which could be performed in various orders: (a) separation based on higher hydrophobicity, such as binding to any hydrophobic matrix/resin; (b) separation based on digestion with a suitable endo- or exo-glucanase or combination thereof, wherein the O-acetylated β-1,6-glucan is resistant to digestion; (c) affinity separation using antibodies or other moieties that bind to β-1,6-glucan or to O-acetyl groups thereon; (d) separation based on molecular weight. In one embodiment, β-1,6-glucan is digested with an enzyme that digests unacetylated and/or lightly acetylated β-1,6-glucan. The resulting material is separated based on size or molecular weight and a portion comprising heavily acetylated glucan is isolated. In some embodiments, β-1,6-glucan preparations are obtained, digested and O-acetylated oligosaccharides are separated or in another embodiment, isolated, and used in the preparation of new compositions. Such compositions represent embodiments of the β-1,6-glucan preparations enriched for O-acetylated residues of this invention.

It is to be understood that the products of any process for preparing enriched O-acetylated β-1,6-glucan preparations are to be considered as appropriate for use in the methods and kits of this invention.

In some embodiments, the glucans for use in the kits and/or according to the methods of this invention may comprise structural modifications, not present in native glucan preparations. Such modifications may comprise, O-acetylation, as described herein. In other embodiments, such modifications may comprise methylation, alkylation, alkoylation, sulfation, phosphorylation, lipid conjugation or other modifications, as are known to one skilled in the art. In some embodiments the modification comprises modification (e.g., esterification) with an acid such as formic, succinic, citric acid, or other acid known in the art.

In some embodiments, lipid conjugation to any or all free hydroxyl groups may be accomplished by any number of means known in the art, for example, as described in Drouillat B, et al., Pharm Sci. 1998 January; 87(1):25-30, B. N. A. Mbadugha, et al., Org. Lett., 5 (22), 4041-4044, 2003.

In some embodiments, methylation may be accomplished and verified by any number of means known in the art, for example, as described in Mischnick et al. 1994 Carbohydr. Res., 264, 293-304; Bowie et al. 1984, Carbohydr. Res., 125, 301-307; Sherman and Gray 1992, Carbohydr. Res., 231, 221-235; Stankowski and Zeller 1992, Carbohydr. Res., 234, 337-341; Harris, P. J., et al. (1984) Carbohydr. Res. 127, 59-73; Carpita, N. C. & Shea, E. M. (1989) Linkage structure of carbohydrates by gas chromatography-mass spectrometry (GC-MS) of partially methylated alditol acetates. In Analysis of Carbohydrates by GLC and MS (Biermann, C. J. & McGinnis, G. D., eds), pp. 157-216. CRC Press, Boca Raton, Fla.

In some embodiments, methylation can be confirmed by GLC of further-derived TMS ethers, acetates or other esters, coupled MS, or digestion to monosaccharides, de-O-methylation and analysis by derivatization and GLC/MS, for example as described in Pazur 1986, Carbohydrate Analysis—A Practical Approach, IRL Press, Oxford, pp. 55-96; Montreuil et al. 1986, Glycoproteins. In M. F. Chaplin and J. F. Kennedy, (eds.), Carbohydrate Analysis—a Practical Approach, IRL Press, Oxford, pp. 143-204; Sellers et al. 1990, Carbohydr. Res., 207, C1-C5; O'Neill et al. 1990, Pectic polysaccharides of primary cell walls. In P. M. Dey (ed.), Methods in Plant Biochemistry, Volume 2, Carbohydrates, Academic Press, London, pp. 415-441; Stephen et al. 1990, Methods in Plant Biochemistry, Volume 2, Carbohydrates, Academic Press, London, pp. 483-522; or Churms 1991, CRC Handbook of Chromatography. Carbohydrates, Volume II, CRC Press, Boca Raton, Fla., USA).

In some embodiments, phosphorylation, optionally including the introduction of other modifications, and verification of the obtained product may be accomplished by means well known to those skilled in the art, see for example, Brown, D. H., Biochem. Biophys. Acta, 7, 487 (1951); Roseman, S., and Daffner, I., Anal. Chem., 28, 1743 (1956); Kornberg, A., and Horecker, B. L., in Methods in enzymology, Vol. I, Academic Press, New York, 1955, p. 323; U.S. Pat. No. 4,818,752.

In some embodiments, glucan sulfation and verification of the obtained product may be accomplished by any of the means well known in the art, for example, as described in Alban, S., and Franz, G. (2001), Biomacromolecules 2, 354-361; Alban, et al. (1992) Arzneimittelforschung 42, 1005-1008; or Alban, S., et al. (2001). Carbohydr. Polym. 47, 267-276.

Also provided by the invention is use of a micelle comprising β-1,6-glucan. In certain embodiments the micelle comprises a complex composed of surfactant molecules comprising β-1,6-glucan, which may be dispersed in a liquid colloid. In certain embodiments the surfactant molecules are amphilic, i.e., they contain both hydrophobic groups (their "tails") and hydrophilic groups (their "heads"). In certain embodiments the hydrophilic component comprises β-1,6-glucan, optionally modified according to any one or more ways described herein. In certain embodiments a micelle in aqueous solution forms an aggregate with the hydrophilic "head" regions in contact with surrounding solvent, sequestering the hydrophobic tail regions in the micelle center. The micelle may be globular and roughly spherical in shape, but in certain embodiments the micelle is an ellipsoid, cylinder, or bilayer. In some embodiments the micelle is a polymeric micelle such as those described in U.S. Pub. No. 20020035217. In some embodiments the micelle encapsulates an active agent, e.g., a hydrophobic molecule. Exemplary active agents include anti-infective agents such as antibacterial, anti-viral, anti-fungal, anti-parasite agents; chemotherapeutic agents for treatment of cancer; a cytokine, antigen, etc.

The invention further provides β-1,6-glucan that is modified by conjugating a lipid thereto, wherein the modification in some embodiments allows for creation of a micelle comprising β-1,6-glucan having the lipid attached thereto. The lipid may be a straight chain or branched, optionally substituted, hydrocarbon. In some embodiments the lipid comprises a fatty acid. In some embodiments the lipid, e.g., fatty acid, contains between 4 and 26 or between 4 and 40 carbon atoms.

Also provided by the present invention is use of or a kit including a particle comprising β-1,6-glucan covalently or noncovalently linked to a particle comprising or consisting essentially of yeast glucan. Also provided is β-1,6-glucan comprising a reactive moiety able to react with a functional group of a yeast glucan to form a covalent bond. The yeast glucan may comprise β-1,6-glucan, β-1,3-glucan, other glucans, or a combination thereof.

In another embodiment, this invention provides a diagnostic kit for determining a subject's responsiveness to a glucan-based vaccine or adjuvant, said kit comprising:
  a glucan which corresponds to or is homologous to glucan in said vaccine or adjuvant;
  reagents for detecting relative immunoglobulin G (IgG) 1, 2, 3 and 4 isotype titers in a subject sample; and
  optionally a series of standards derived from positive and negative responders to said glucan-based vaccine or adjuvant.

According to this aspect of the invention, and in one embodiment, the glucan is attached to a substrate, which in one embodiment is a microtiter plate or in another embodiment is a bead. In one embodiment, the reagents comprise a detectable marker which renders the detection semi-quantitative.

In some embodiments, the subject has been exposed to environmental glucans, and the diagnostic is for determining responsiveness of the subject to a particular glucan-based vaccine. According to this aspect, the kit will comprise a glucan which corresponds to or is a fragment of, or is highly homologous to the glucan in the vaccine for which responsiveness is being determined.

According to this aspect, and in one embodiment, the term "homology", when in reference to a glucan as herein described, indicates a percentage of structural identity or identity in terms of composition or content in the candidate molecule as compared to a corresponding glucan reference molecule.

In one embodiment, the terms "homology", "homologue" or "homologous", in any instance, indicate that the molecule referred to, exhibits at least 70% correspondence with the reference molecule. In another embodiment, the glucan molecule exhibits at least 72% correspondence with the reference molecule. In another embodiment, the glucan molecule exhibits at least 75% correspondence with the reference molecule. In another embodiment, the glucan molecule exhibits at least 77% correspondence with the reference molecule. In another embodiment, the glucan molecule exhibits at least 80% correspondence with the reference molecule. In another embodiment, the glucan molecule exhibits at least 82% correspondence with the reference molecule. In another embodiment, the glucan molecule exhibits at least 85% correspondence with the reference molecule. In another embodiment, the glucan molecule exhibits at least 87% correspondence with the indicated sequence. In another embodiment, the glucan molecule exhibits at least 90% correspondence with the reference molecule. In another embodiment, the glucan molecule exhibits at least 92% correspondence with the reference molecule. In another embodiment, the glucan molecule exhibits at least 95% or more correspondence with the reference molecule. In another embodiment, the glucan molecule exhibits at least 95%-100% correspondence to the reference molecule.

With regard to correspondence to a reference molecule, such correspondence may refer to structural identity or compositional identity, in terms of chemical content. In some embodiments, similarly prepared glucans are utilized in kits of this invention, which are comparable to those utilized in a glucan-based adjuvant or vaccine, however the glucan utilized in the kit may not have been subjected to all processing steps, which comprise the preparation process for a glucan-based vaccine or adjuvant.

Homology may be determined, in one embodiment, by methods well described in the art, including immunoblot analysis, or via computer algorithm analysis of, utilizing any of a number of software packages available, via established methods.

Also provided by the invention is a kit comprising or use of a composition comprising β-1,6-glucan and a biodegradable polymer. In some embodiments the biodegradable polymer comprises biologically active subunits. The term "biodegradable" refers, in some embodiments, to a material, which is degraded, i.e., broken down into smaller fragments, in the biological environment of the cell or subject in which it is found. In one embodiment, biodegradation involves the degradation of a polymer into its component subunits, via, for example, enzymatic or non-enzymatic hydrolysis, digestion, etc. In one embodiment, biodegradation may involve cleavage of bonds (whether covalent or otherwise) in the polymer backbone. In another embodiment, biodegradation may involve cleavage of a bond (whether covalent or otherwise) internal to a side-chain or one that connects a side chain to the polymer backbone. In some embodiments the degradation products are metabolizable by the subject. In some embodiments the degradation products are usable by the subject for synthesis of larger biomolecules. In some embodiments the degradation products are excreted or otherwise eliminated by the subject. In some embodiments the polymer and/or its degradation products are biocompatible in that they are substantially nontoxic and do not produce an unacceptable inflammatory or immune response when administered or otherwise introduced into the body of a subject in amounts consistent with the present invention.

The term "biologically active agent" includes, in some embodiments, therapeutic agents that provide a therapeutically desirable effect when administered to an animal (e.g., a mammal, such as a human) in effective amounts, it being understood that not all subjects will benefit from the agent. In some embodiments the polymer is a polyanhydride, which optionally comprises biologically active salicylates and alpha-hydroxy acids. Degradation of the polymer releases said biologically active salicylates and/or alpha-hydroxy acids. In some embodiments the β-1,6-glucan is covalently or noncovalently attached to the biodegradable polymer. Suitable polymers and methods for manufacture thereof are described, e.g., in U.S. Publication No. 20030035787 and 20050053577. In certain embodiments the polymer comprises between 10 and 1000, or between 50 and 500, or about 100 monomers. In one embodiment the polymer is Polyaspirin®. Methods of forming a compound in which a β-1,6-glucan is covalently linked to the polymer will be evident to one of skill in the art. The β-1,6-glucan could be covalently attached to a monomer prior to polymerization or could be conjugated to a functional group of the polymer following polymerization. In some embodiments the β-1,6-glucan is covalently attached via a linking group. Exemplary linking groups are described in U.S. Pub. No. 20050053577, and others will be evident to one of skill in the art.

In some embodiments the kits comprise and methods make use of a particle comprising β-1,6-glucan and the biodegradable polymer. In some embodiments the particle is coated with or impregnated with β-1,6-glucan. In some embodiments the β-1,6-glucan is covalently attached to the polymer. In some embodiments the composition coats an implant or other medical or surgical device as described elsewhere herein.

Further provided are methods of administering a β-1,6-glucan and a biologically active salicylate or alpha-hydroxy acid to a subject, the method comprising administering a composition comprising β-1,6-glucan and a biodegradable polymer comprising said biologically active salicylates and/or alpha-hydroxy acids to the subject or implanting or introducing a device comprising said polymer and said biologically active salicylates and/or alpha-hydroxy acids into a subject.

In some embodiments, this invention provides kits comprising and methods making use of low molecular weight glucans, having a molecular weight of less than 100 kDa (e.g., less than 80, 70, 60, 50, 40, 30, 25, 20, or 15 kDa). In some embodiments, this invention provides oligosaccharides e.g., containing 85 or fewer (e.g., 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4) glucose monosaccharide units.

In some embodiments the β-1,6-glucan used in the kits or methods of this invention comprises or consists essentially of a low molecular weight glucan. In some embodiments of any method of the invention in which β-1,6-glucan is utilized, the β-1,6-glucan comprises or consists essentially of a low molecular weight glucan. Optionally at least some of the low molecular weight β-1,6-glucan in any embodiment of the invention is enriched for O-acetylated groups.

A common technique in determining linkage type and structure in glucans is carbon-13 nuclear magnetic resonance spectroscopy (13 C-NMR). The number and relative intensities of $^{13}C$ signals in a given spectrum can be used to determine linkage configurations and positions in glucan polymers. For example, the chemical shifts (signals) of carbon atoms engaged in the glycosidic bond are shifted strongly downfield (up to 9 ppm) compared to the corresponding unlinked carbons.

This invention provides, in some embodiments, kits and uses of a composition comprising β1-6 glucan, wherein the glucan is conjugated to a solid support. In one embodiment, the solid support is a bead or particle.

In one embodiment, the beads or particles or substrates to which glucans are conjugated comprise denatured proteins (e.g., human serum albumin (Benacerraf et al., 1957 Brit. J. Exp. Path, 38:35)), insoluble materials (e.g., carbon black, silica, silicon dioxide, polystyrene, latex), metal oxides (e.g., titanium oxides, iron oxides), and India ink (i.e., suspension of colloidal carbon particles) (described in Reichard and Filkins, 1984, The Reticuloendothelial System; A Comprehensive Treatise, pp. 73-101 (Plenum Press), and references therein), hydrogels, (for example as described in US Patent Publication No. 20050191361), sepharose or agarose beads or microparticles. In some embodiments the beads or microparticles are formed from materials that are biodegradable and non-toxic (e.g., a poly(α-hydroxy acid) such as poly (lactide-co-glycolide), a polyhydroxybutyric acid, a polyorthoester, a polyanhydride, a polycaprolactone, etc.). The beads or particles of the present invention may comprise red blood cells (RBCs) that have been purged of their cytoplasm, known as 'Ghost' RBCs, bacteria (as bacteria are cleared by the RES; see, e.g., Benacerraf and Miescher, 1960, Ann NY Acad Sci, 88:184-195), cell fragments, liposomes, bacteriophages, bacteriophage fragments, and viral capsids devoid of the viral nucleic acids (e.g., hepatitis B virus surface antigen particles), etc.

In one embodiment, conjugation to the solid support is via chemically cross-linking the solid to the glucans of this invention. The chemistry of cross-linking is well known in the art. The nature of the crosslinking reagent used to conjugate the glucan and the solid (e.g., bead or particle) can be any suitable reagent known in the art. It is to be understood that any suitable crosslinking agent may be used with care taken that the activity of the glucan is preserved.

The particle may be a fragment of a bacteriophage or bacteria.

In certain embodiments the size of the particle is appropriate for ingestion by macrophages, neutrophils, or both. The particle can have any of the compositions described herein. In certain embodiments the invention provides a population of particles, wherein at least 50% of the particles have a size appropriate for ingestion by macrophages, neutrophils, or both. The invention provides populations of particles, wherein at least 50%, 75%, or 90% of the particles fall within a desired size range. In certain embodiments the desired size ranges within ±10%, ±20%, ±30%, ±40%, or ±50% of a given value. The value may be, e.g., 20 nm, 100 nm, 500 nm, 1, 5, 10, 20, 50 microns, etc. The particles in any of these embodiments can have any of the compositions described herein. The population can comprise particles having different compositions, in any ratio. The populations of particles may be used for any of the purposes described herein, and methods for such use are an aspect of this invention.

Cross-linking reagents that can be used include but are not limited to p-Azidobenzoyl hydrazide, N-(4-[p-Azidosalicylamido]-butyl)-3'(2'-pyridyldithio)-propionamide, Bis (beta-[4-azidosalicylamido]-ethyl)disulfide, 1,4-bismaleimidyl-2,3-dihydroxybutane, 1,6-Bismaleimidohexane, 1,5-Difluoro-2,4-dinitrobenzene, Dimethyl adipimidate-2HCl, Dimethyl suberimidate-2HCl, Dimethyladipodimidate-2HCl, Dimethyl pimelimidate-2HCl, Disuccinimidyl glutarate, Disuccinimidyl tartrate, 1-Ethyl-3-[3-Dimethylanonopropyl]Carbodiimide Hydrochloride, (N-Hydroxy succinimidyl)-4-Azidosalicylic acid, Sulfosuccinmidyl 2-[7-azido-4-methyl-coumarin-3-acetamidomethyl-1,3-aminopropionate, N-Succinimidyl-4-iodoacetylaminobenzoate, N-Succinimidyl-3-[2-pyridylthio]propionate, and Succinimidyl 6-[3-(2-pyridylathio)-propionamide]hexanoate (Pierce Chemical Co., Rockford, Ill.) In one embodiment, the glucans are derivatized as described in Nature Methods Vol 2 No. 11, p., 845, 2005, or a similar approach. In one embodiment glucans are derivatized with a moiety that provides a free, reactive primary amine using a reagent such as 2,6-diaminopyridine (DAP). The Schiff base azomethine can be reduced, e.g., by sodium cyanoborohydride to a stable secondary amine. In one embodiment, the derivatized glucan is then reacted with an N-hydroxysuccinimide (NHS) ester, such as NHS-biotin.

Other crosslinking reagents comprise aldehyde, imide, cyano, halogen, carboxyl, activated carboxyl, anhydride and maleimide functional groups. In some embodiments, the cross-linking reagent may comprise heterobifunctional crosslinking reagents such as ABH, M2C2H, MPBH and PDPH (Pierce Chemical Co., Rockford, Ill.). See, e.g., Hermanson, G. T. (1996). Bioconjugate Techniques, Academic Press, Inc., for further discussion of cross-linking methods and reagents.

In another embodiment, conjugation of the glucan to the beads or particles may be via use of beads comprising functional groups which can be conjugated according to methods as disclosed by, e.g., Brumeanu et al. (Genetic Engineering News, Oct. 1, 1995, p. 16).

It is also possible to conjugate the beads/particles/solid support to the glucan by non-covalent means. One convenient way for achieving non-covalent conjugation comprises utilizing antibodies to the glucan, which are covalently or non-covalently attached to the particle, bead, etc. In another embodiment, non-covalent conjugation is achieved using biotin-avidin (where "avidin" should be understood to refer to any form of avidin). For example, avidin-coated or conjugated beads may be contacted with glucan derivatized with a biotin moiety.

In some embodiments, preparation of the conjugated glucans includes purification of the final conjugate substantially free of unconjugated reactants. Purification may be achieved by affinity, gel filtration, hydrophobic chromatography, tangential ultrafiltration, diafiltration or ion exchange chromatography based on the properties of either component of the conjugate. For example, purification may reduce the amount of one or more of the unconjugated reactants (e.g., glucan or solid support) to 10% or less, 5% or less, or 1% or less of the amount of unconjugated reactant that was originally present.

In some embodiments, the invention provides a particle comprising β1-6 glucan, which in some embodiments, is enriched for O-acetylated groups. In some embodiments, the particle comprises at least 50% β1-6 glucan by weight. In some embodiments, the β1-6 glucan is homogeneously distributed in the particle. It is to be understood that the particles comprising β1-6 glucan of this invention, may in turn encompass any embodiment appropriate thereto, as described herein.

In one embodiment, the conjugated glucan is enriched for O-acetylated groups, and in one embodiment, contains at least 25% by weight O-acetylated glucan, or any related embodiment as herein described. In one embodiment, the glucan is conjugated to a microsphere, which in one embodiment, has a diameter of about 1-100 microns. In one embodiment, the microsphere has a diameter which ranges from about 10-50 microns. In another embodiment, the microsphere has a diameter which ranges from about 5-40 microns. In another embodiment the diameter ranges from 0.1 to 5 microns. In another embodiment the diameter ranges from 0.5 to 1 micron. In another embodiment, the particle or bead is in the nanometer range, e.g., 100 to 500 nm.

In one embodiment, the term "bead" or "particle" or "solid support" refers to a material, which is spherical. In another embodiment, term "bead" or "particle" or "solid support" refers to a material, which is non-spherical. In one embodiment, non-spherical beads or particles possess a longest axis or longest dimension between any two points on their surface within any of the afore-mentioned ranges. In one embodiment, the dimensions of the particle (e.g., diameter) are selected to promote phagocytosis of the particles by phagocytic cells, such as neutrophils, macrophages or dendritic cells.

In one embodiment, the term "bead" or "particle" or "solid support" refers to any solid or gelled, or sol-gel-based material, to which the glucan can be adhered, of a size and composition, which can be taken up by phagocytic cells.

In one embodiment, the kits/compositions of this invention comprise or methods of this invention make use of beads or particles having dimensions and surface density of glucan (e.g., β-1,6 glucan, optionally enriched for O-acetylated groups), that is efficiently phagocytosed by antigen presenting cells as compared, e.g., with particles having different dimensions and/or surface density of glucan.

In one embodiment, conjugation to the solid support may be accomplished with a direct linkage via reaction with solid supports comprising a reactive functional group.

Linkages via a linker group may be made using any known procedure, for example, the procedures described, for example, in U.S. Pat. Nos. 6,642,363; 4,882,317; or 4,695,624. A useful type of linkage is an adipic acid linker, which may be formed by coupling a free —NH2 group on an aminated glucan with adipic acid (using, for example, diimide activation), and then coupling a protein to the resulting saccharide-adipic acid intermediate. Another type of linkage is a carbonyl linker, which may be formed by reaction of a free hydroxyl group of a modified glucan with CDI followed by reaction with a protein to form a carbamate linkage. Other linkers include B-propionamido, nitrophenyl-ethylamine, haloacyl halides, glycosidic linkages, 6-aminocaproic acid, ADH, C4 to C12 moieties, etc.

In another embodiment, the invention provides a particle comprising β1-6 glucan. In certain embodiments, the particle consists of at least 10%, 20%, 30%, 40%, 50%, 60%, 70%, 80%, 90%, 95%, 96%, 97%, 98%, or 99% β1-6 glucan by dry weight. In certain embodiments, the particle consists essentially of β1-6 glucan. In certain embodiments, the particle consists essentially of β1-6 glucan, exclusive of any solvent component, such as water. In certain embodiments the β1-6 glucan is enriched for O-acetylated groups. In certain embodiments the particle contains less than 50%, 40%, 30%, 20%, 10%, or 5% β-3 glucan by dry weight. The invention further provides a composition containing any of the aforementioned particles comprising or consisting essentially of β1-6 glucan, optionally enriched for O-acetylated groups. The composition may further contain a pharmaceutically acceptable carrier or adjuvant. The invention further provides a method of modulating the immune response of a mammalian subject comprising administering any of the afore-mentioned particles, or a composition containing any of the aforementioned particles, to the subject. The particle can be prepared using any method known in the art. The particles can be milled or sieved to achieve a desired size. In certain embodiments the β1-6 glucan is distributed evenly, or homogeneously, in the particle. In certain embodiments "distributed evenly" means that the β1-6 glucan is not encapsulated within a different material, does not simply coat the surface of a particle comprised of a different material, or is not covalently or non-covalently attached to the surface of a particle composed of a different material. Instead, in certain embodiments the β1-6 glucan, optionally mixed with another material, is formed into a particle such that the β1-6 glucan is located throughout substantially the entire volume of the particle. It will be appreciated that the density of the β1-6 glucan may vary but will generally vary gradually and continuously throughout the particle rather than abruptly.

In another embodiment, this invention provides a β1-6 glucan conjugated to a solid support, wherein the solid support is a substrate, on or in which it is useful to conduct an assay. For example, and in some embodiments, the kits/methods of this invention make use of a microtiter plate, or 96 well plate to which a β1-6 glucan has been adhered, and an assay is conducted within the wells/plate. Such substrates may comprise any suitable material, for example, being resistant to solvents, being transparent such that spectrophotometry may be conducted on the samples within the substrate.

In some embodiments, the β1-6 glucan for use in methods of this invention may further comprise a targeting moiety. In some embodiments, the targeting moiety is for a particular cell type, or in some embodiments, a diseased cell such as, for example, an infected cell, or a neoplastic cell or a preoplastic cell. In some embodiments, for example, targeting of a virally infected cell may be accomplished via linkage of the glucan with a viral co-receptor. In some embodiments, targeting moieties may include integrins or class II molecules of the MHC, which may be upregulated on infected cells such as professional antigen presenting cells.

In some embodiments, targeting of an infected cell results in enhanced therapeutic responses to infection in the subject. For example, and in some embodiments, targeting the infected cell enhances phagocytosis and/or cytotoxic responses to the pathogen, or in some embodiments, enhances complement-mediated lysis of the pathogen. In some embodiments, targeting of the infected cell enhances the immune response to the pathogen.

In some embodiments, the targeting moiety specifically interacts with a neoplastic or preneoplastic cell, as described herein, and comprising any embodiment thereof. In some embodiments, the use of a β1-6 glucan linked to a targeting moiety, which targets a neoplastic or preneoplastic cell promotes host anticancer responses. In some embodiments, such targeting promotes tumor cell lysis, or in some embodiments, enhances host anti-tumor responses.

In some embodiments, and without limitation, use of the glucans, β1-6 glucan linked to a targeting moiety and/or compositions of this invention target the polysaccharide to an antigen expressed specifically on cancer cells and thereby enhance complement-mediated lysis of the cells.

In one embodiment, this invention provides a method of stimulating an immune response in a subject, comprising administering to the subject purified β-1-6-glucan and an agent, which biases antibody production to yield relatively greater amounts of immunoglobulin G (IgG) 1, 2 or 3 versus immunoglobulin G (IgG) 4.

According to this aspect of the invention, and in one embodiment, the subject is administered the purified β-1-6-glucan and the agent concurrently, or in another embodiment the subject is administered purified β-1-6-glucan and the agent sequentially. In another embodiment the subject is administered said purified β-1-6-glucan and said cytokine each at least two times.

In one embodiment, the agent is a cytokine, which in one embodiment is interleukin-2, interleukin-12 or interferon-γ or a combination thereof. In another embodiment, the agent downmodulates interleukin-4 or interleukin-10 production or interferes with interleukin-4 or interleukin-10 activity.

In one embodiment, the subject is further exposed to an antigen associated with a target of the immune response, which in one embodiment is a tumor-associated antigen. According to this aspect of the invention, and in one embodiment, the subject has a hyperplastic or preneoplastic lesion, and in another embodiment, the method treats, delays progression of, prolongs remission of, or reduces the incidence or severity of cancer in the subject. In another embodiment, the subject has cancer. In another embodiment, the subject has not been diagnosed with cancer. In another embodiment, the subject has not been diagnosed with a tumor.

In another embodiment, the antigen is derived from a pathogen, which in one embodiment is a fungus. In one embodiment, the method treats, delays progression of, prolongs latency of, or reduces the incidence or severity of infection in the subject.

In some embodiments, the method comprising targeting the βglucan and optionally the cytokine to neoplastic or preneoplastic cells or tissue, or tumors, which can be accomplished by targeting a tumor antigen, as herein described. In some embodiments, such cells may express adrenomedullin receptors (ADMR), a calcitonin receptor-like receptor (CRLR), CD117 or any combination of tumor associated antigens, as herein described.

According to this aspect, and in one embodiment, by targeting cells expressing adrenomedullin receptors with the linked glucans of this invention, lung, pancreas, ovary, and other related cancers may be treated. In some embodiments, by targeting cells expressing CRLR and/or CD117, with the linked glucans of this invention, vascular tumors, gliomas, and/or other related cancers may be treated.

In some embodiments, reference herein to a targeting moiety is to be understood to encompass an antibody, or fragment thereof as described herein, a naturally occurring peptide ligand for the referenced receptor, or a modified form thereof, such as, for example, a truncation product. In some embodiments, reference herein to a targeting moiety is to be understood to encompass artificial peptides, small molecules, and the like.

In some embodiments, this invention provides for the use of the glucans, β1-6 glucans linked to a targeting moiety and/or compositions of this invention (as described herein, including any embodiment thereof) as a means to determine neoplastic or preneoplastic cell or tissue responsiveness to a treatment regimen. In some embodiments, such method includes obtaining a tumor sample from the subject or biopsy material containing the neoplastic or preneoplastic cells and assessing the sensitivity or resistance of the cells to in vitro lysis and/or determining the level of expression and/or secretion of an endogenous complement control protein.

In some embodiments the tumor cell expresses or overexpresses (e.g., relative to a normal cell of the cell type or tissue of origin of that cell) an endogenous complement control protein such as complement receptor 1 (CR1 or CD35), decay-accelerating factor (DAF or CD55), membrane cofactor protein (MCP of CD46), complement factor H (1H) (or FHL-1) and/or C4b-binding protein (C4BP).

In some embodiments, this invention provides for the use of the glucans, β1-6 glucans linked to a targeting moiety and/or compositions of this invention (as described herein, including any embodiment thereof) as a means to target pathological vasculature, such as, for example, atherosclerotic vasculature, or in some embodiments, targeting pathologic neo-vasculature such as tumor-associated neovasculature for purposes of enhancing elimination of such vasculature.

According to this aspect of the invention and in some embodiments, the targeting moiety comprises, inter alia, an antibody or antibody fragment or ligand specifically interacting with a component of such vasculature, for example, an agent specifically interacting with VEGF, tissue factor, a clotting factor, vascular cell adhesion molecules, integrins, selectins, or any other marker expressed on or at the surface of endothelial cells.

In one embodiment, the targeting moiety is a peptide, an antibody, an antibody fragment, a receptor, Protein A, Protein G, biotin, avidin, streptavidin, a metal ion chelate, an enzyme cofactor, a nucleic acid or a ligand.

In some embodiments, such a targeting moiety may comprise an antibody or antibody fragment. In some embodiments, such antibody or antibody fragment will specifically interact with a desired target, as described herein, and linkage of said antibody or fragment with the glucan does not inhibit such interaction.

In some embodiments, the term "antibody" refers to intact molecules as well as functional fragments thereof, such as Fab, F(ab')2, and Fv that are capable of specifically interacting with a desired target, as described herein. In some embodiments, the antibody fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

In some embodiments, the antibody fragments may be prepared by proteolytic hydrolysis of the antibody or by expression in E. coli or mammalian cells (e.g., Chinese hamster ovary cell culture or other protein expression systems) of DNA encoding the fragment.

Antibody fragments can, in some embodiments, be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

In some embodiments, the antibodies or fragments as described herein may comprise "humanized forms" of antibodies. In some embodiments, the term "humanized forms of antibodies" refers to non-human (e.g., murine) antibodies, which are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

In one embodiment, the targeting moiety is an antibody or fragment thereof, specifically recognizing a neutrophil, for example, and antibody specifically recognizing L-selectin, β2-integrins, complement receptor 1 (CR-1), decay-accelerating factor (DAF), C5a receptor, intercellular adhesion molecule-1 (ICAM-1), ICAM-3 and others as will be appreciated by one skilled in the art.

In some embodiments, phagocytic cells are targeted by a molecule interacting with Fc receptors, chemokine receptors, CD40, CD80, CD86, MHC class II molecules, CD69, ADAMS, CD14, CD163, CD33, CD63, CD68, CD74, CHIT1, CHST10, CSF1R, DPP4, FABP4, FCGR1A, ICAM2, IL1R2, ITGA1, ITGA2, S100A8, TNFRSF8, and others as will be appreciated by one skilled in the art.

In another embodiment, the targeting moiety may be any appropriate moiety, for example, aptamers, naturally occurring or artificial ligands, or engineered binding proteins may comprise the targeting moieties as described herein, and their physical association with a glucan as herein described can be readily accomplished by any number of means known in the art, including, for example, the methods described hereinbelow, or variations thereof, to suit the particular nature of the targeting moiety chosen.

In one embodiment, the targeting moiety enhances attachment to the cell, or, in another embodiment, enhances homing to the cell. In one embodiment, the targeting moiety enhances attachment following supply of an energy source. In one embodiment, the targeting moiety is chemically attached to the glucan via a chemical cross-linking group, or in another embodiment, forms a stable association with the glucan, or, in another embodiment, forms an association with the glucan, which dissociates following changes in environmental conditions, such as, for example, salt concentration or pH.

In one embodiment, the targeting moiety may be an antibody, which specifically recognizes a molecule of interest, such as a protein or nucleic acid. In another embodiment, the antibody may specifically recognize a reporter molecule attached to a molecule of interest. In another embodiment, the targeting moiety may be an antibody fragment, Protein A, Protein G, biotin, avidin, streptavidin, a metal ion chelate, an enzyme cofactor, or a nucleic acid. In another embodiment, the targeting moiety may be a receptor, which binds to a cognate ligand of interest, or associated with a cell or molecule of interest, or in another embodiment, the targeting moiety may be a ligand which is used to attach to a cell via interaction with its cognate receptor.

Linking the targeting moiety to the glucan of this invention may be accomplished by any means known in the art, for example as described further herein in Example 7, or for example, as described in U.S. Pat. No. 5,965,714, or United States Patent Publication No. 20070141084, or Schneerson et al., Proc Natl Acad Sci USA. 2003 Jul. 22; 100 (15):8945-50, Lees et al., Vaccine. 1996 February; 14 (3):190-8, or via the use of a cross-linking agent as described herein, or other methods, as will be appreciated by one skilled in the art.

In some embodiments, glycosylated antibodies are used and the B-1,6-glucan is linked to the glycosylated residue of the antibody, or in another embodiment, linkages may be multiple and involve multiple sites on the antibody, or targeting moiety, as will be understood by one skilled in the art.

In some embodiments, linking the glucan to a targeting moiety results in enhanced phagocytosis and/or killing of the targeted cell or organism. In some embodiments, such lysis may be mediated by any professional antigen presenting cell or killer cell, such as, for example, neutrophils, macrophages, dendritic cells, natural killer cells, cytotoxic T lymphocytes, and others.

In some embodiments, any O-acetylated glucan may be physically associated with a targeting moiety, and comprise the glucans or compositions of this invention, representing an embodiment thereof. Use of such O-acetylated glucans, for example β-1,3-glucans which have been O-acetylated, for modulating immune responses, treating cancer or precancerous lesions, promoting resolution of infection, or any method as herein described is to be considered as part of this invention.

In some embodiments, any of the glucan preparations of the kits and for use in the methods of this invention may be linked to a labeling agent, such that detection of the glucan is readily accomplished. In one embodiment, the term "a labeling agent" refers to a molecule which renders readily detectable that which is contacted with a labeling agent. In one embodiment, the labeling agent is a marker polypeptide. The marker polypeptide may comprise, for example, green fluorescent protein (GFP), DS-Red (red fluorescent protein), secreted alkaline phosphatase (SEAP), beta-galactosidase, luciferase, or any number of other reporter proteins known to one skilled in the art. In another embodiment, the labeling agent may be conjugated to another molecule which provides greater specificity for the target to be labeled. For example, and in one embodiment, the labeling agent is a fluorochrome conjugated to an antibody which specifically binds to a given target molecule, or in another embodiment, which specifically binds another antibody bound to a target molecule, such as will be readily appreciated by one skilled in the art. In some embodiments, the glucan linked to an antibody incorporates a fluorochrome in the antibody as will be appreciated by one skilled in the art.

In one embodiment, this invention provides for the combined use of, or compositions comprising β-glucans and an adjuvant, or when β-glucan based adjuvants are used, a second adjuvant is administered with the β-glucan. In some embodiments, the adjuvant may include, but is not limited to: (A) aluminium compounds (e.g., aluminium hydroxide, aluminium phosphate, aluminium hydroxyphosphate, oxyhydroxide, orthophosphate, sulphate, etc. [e.g., see chapters 8 & 9 of ref. 96]), or mixtures of different aluminium compounds, with the compounds taking any suitable form (e.g., gel, crystalline, amorphous, etc.), and with adsorption being preferred; (B) MF59 (5% Squalene, 0.5% Tween 80, and 0.5% Span 85, formulated into submicron particles using a microfluidizer); (C) liposomes; (D) ISCOMs, which may be devoid of additional detergent; (E) SAF, containing 10% Squalane, 0.4% Tween 80, 5% pluronic-block polymer L121, and thr-MDP, either micro fluidized into a submicron emulsion or vortexed to generate a larger particle size emulsion; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21, also known as Stimulon™; (H) chitosan; (I) complete Freund's adjuvant (CFA) and incomplete Freund's adjuvant (IFA); (J) cytokines, such as interleukins (e.g., IL-1, IL-2, IL-4, IL-5, IL-6, IL-7, IL-12, etc.), interferons (e.g., interferon-γ), macrophage colony stimulating factor, tumor necrosis factor, etc.; (K) monophosphoryl lipid A (MPL) or 3-O-deacylated MPL (3dMPL)]; (L) combinations of 3dMPL with, for example, QS21 and/or oil-in-water emulsions; (M) oligonucleotides comprising CpG motifs] i.e., containing at least one CG dinucleotide, with 5-methylcytosine optionally being used in place of cytosine; (N) a polyoxyethylene ether or a polyoxyethylene ester; (O) a polyoxyethylene sorbitan ester surfactant in combination with an octoxynol or a polyoxyethylene alkyl ether or ester surfactant in combination with at least one additional non-ionic surfactant such as an octoxynol; (P) an immuno-stimulatory oligonucleotide (e.g., a CpG oligonucleotide) and a saponin; (Q) an immuno-stimulant and a particle of metal salt; (R) a saponin and an oil-in-water emulsion; (S) a saponin (e.g., QS21)+3dMPL+IL12 (optionally+a sterol); (T) E. coli heat-labile enterotoxin ("LT"), or detoxified mutants thereof, such as the K63 or R72 mutants; (U) cholera toxin ("CT"), or diphtheria toxin ("DT") or detoxified mutants of either; (V) double-stranded RNA; (W) monophosphoryl lipid A mimics, such as aminoalkyl glucosaminide phosphate derivatives e.g., RC-529]; (X) polyphosphazene (PCPP); or (Y) a bioadhesive such as esterified hyaluronic acid microspheres or a mucoadhesive such as crosslinked derivatives of poly(acrylic acid), polyvinyl alcohol, polyvinyl pyrollidone, polysaccharides and carboxymethylcellulose.

Muramyl peptides include N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)ethylamine MTP-PE), etc.

In another embodiment, this invention provides for the combined use of β-glucans, an agent, which biases antibody production to yield relatively greater amounts of immunoglobulin G (IgG) 1, 2 or 3 versus immunoglobulin G (IgG) 4 and an antigen.

In various embodiments, the antigen may be any molecule recognized by the immune system of the subject as foreign. For example, the antigen may be any foreign molecule, such as a protein (including a modified protein such as a glycoprotein, a mucoprotein, etc.), a nucleic acid, a carbohydrate, a proteoglycan, a lipid, a mucin molecule, or other similar molecule, including any combination thereof. The antigen may, in another embodiment, be a cell or a part thereof, for example, a cell surface molecule. In another embodiment, the antigen may derive from an infectious virus, bacteria, fungi, or other organism (e.g., protists), or part thereof. These infectious organisms may be active, in one embodiment or inactive, in another embodiment, which may be accomplished, for example, through exposure to heat or removal of at least one protein or gene required for replication of the organism. In one embodiment, the antigenic protein or peptide is isolated, or in another embodiment, synthesized.

In one embodiment, the term "antigen" refers to a substance such as a protein, peptide, or any fragment which stimulates or enhances an immune response, following exposure to or contact with the antigen. In one embodiment, the antigen is a "danger" signal interpreted by the immune system of a subject as to initiate or enhance an immune response as a consequence of the signal. In another embodiment, the antigen represents the host's ability to distinguish the presence of a molecule which is "non-self".

In one embodiment, the antigen is derived from a pathogen, an infected cell, a neoplastic or preneoplastic cell. In another embodiment, the antigen is an autoantigen, or a molecule which initiates or enhances an autoimmune response.

In one embodiment, the antigen is derived from a parasitic agent, which resides intracellularly during at least some stages of its life cycle. The intracellular parasites contemplated include for example, protozoa. Protozoa, which infect cells, include: parasites of the genus Plasmodium (e.g., Plasmodium falciparum, P. Vivax, P. ovale and P. malariae), Trypanosoma, Toxoplasma, Leishmania, Schistosoma, and Cryptosporidium. In another embodiment the parasitic agent resides extracellularly during at least part of its life cycle. Examples include nematodes, trematodes (flukes), and cestodes. In some embodiments, the antigen is derived from byproducts of infection with the protozoa described, for example, egg antigens of the Schistosoma, antigens uniquely expressed from Toxoplasma cysts, and others, as will be appreciated by one skilled in the art.

In one embodiment, the antigen is derived from a diseased and/or abnormal cell. The diseased or abnormal cells contemplated include: infected cells, neoplastic cells, pre-neoplastic cells, inflammatory foci, benign tumors or polyps, cafe au lait spots, leukoplakia, other skin moles, self-reactive cells, including T and/or NK cells, etc In one embodiment, the antigen is derived from an infectious virus including, inter-alia: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

In one embodiment, the antigen is derived from bacteria including, inter-alia: *Helicobacter pylori, Borellia burgdorferi, Legionella pneumophila, Mycobacteria* sps (e.g., *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic sps), *Streptococcus pneumoniae*, pathogenic *Campylobacter* sp., *Enterococcus* sp., *Chlamydia* sp., *Haemophilus influenzae, Bacillus antracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Actinomyces israelli* and *Francisella tularensis.*

In one embodiment, the antigen is derived from fungi, including, inter-alia: *Absidia,* such as *Absidia corymbifera, Ajellomyces,* such as *Ajellomyces capsulatus, Ajellomyces dermatitidis, Arthroderma,* such as *Arthroderma benhamiae, Arthroderma fulvum, Arthroderma gypseum, Arthroderma incurvatum, Arthroderma otae, Arthroderma vanbreuseghemii, Aspergillus,* such as *Aspergillus flavus, Aspergillus fumigatus, Aspergillus niger, Blastomyces,* such as *Blastomyces dermatitidis, Candida,* such as *Candida albicans, Candida glabrata, Candida guilliermondii, Candida krusei, Candida parapsilosis, Candida tropicalis, Candida pelliculosa Cladophialophora,* such as *Cladophialophora carrionii, Coccidioides,* such as *Coccidioides immitis, Cryptococcus,* such as *Cryptococcus neoformans, Cunninghamella, Epidermophyton,* such as *Epidermophyton floccosum, Exophiala,* such *Exophiala dermatitidis, Filobasidiella,* such as *Filobasidiella neoformans, Fonsecaea,* such as *Fonsecaea pedrosoi, Fusarium,* such as *Fusarium solani, Geotrichum,* such as *Geotrichum candidum, Histoplasma,* such as *Histoplasma capsulatum, Hortaea,* such as *Hortaea werneckii, Issatschenkia,* such as *Issatschenkia orientalis, Madurella,* such *Madurella grisae, Malassezia,* such as *Malassezia furfur, Malassezia globosa, Malassezia obtuse, Malassezia pachydermatis, Malassezia restricta, Malassezia slooffiae, Malassezia sympodialis, Microsporum,* such as *Microsporum canis, Microsporum fulvum, Microsporum gypseum, Mucor,* such as *Mucor circinelloides, Nectria,* such as *Nectria haematococca, Paecilomyces,* such as *Paecilomyces variotii, Paracoccidioides,* such as *Paracoccidioides brasiliensis, Penicillium,* such as *Penicillium marneffei, Pichia,* such as *Pichia anomala, Pichia guilliermondii, Pneumocystis,* such as *Pneumocystis carinii, Pseudallescheria,* such as *Pseudallescheria boydii, Rhizopus,* such as *Rhizopus oryzae, Rhodotorula,* such as *Rhodotorula rubra, Scedosporium,* such as *Scedosporium apiospermum, Schizophyllum,* such as *Schizophyllum commune, Sporothrix,* such as *Sporothrix schenckii, Trichophyton,* such as *Trichophyton mentagrophytes, Trichophyton rubrum, Trichophyton verrucosum, Trichophyton violaceum, Trichosporon,* such as *Trichosporon asahii, Trichosporon cutaneum, Trichosporon inkin, Trichosporon mucoides,* or others.

In one embodiment, the pathogenic fungus infects human hosts. In one embodiment the pathogenic fungus infects non-human animals.

In some embodiments, the compositions and methods of this invention allow for the combined use of multiple antigens from the same source, multiple antigens from the same class of organism, multiple antigens from different classes of organisms, or any combination thereof.

In another embodiment, this invention provides a method of treating, delaying progression of, or reducing the incidence or severity of an infection in a subject, said method comprising administering to said subject a composition comprising purified β-1-6 glucan. In certain embodiments of the invention the infection is one due to a pathogenic fungus. In certain embodiments of the invention the infection is one due to a pathogenic bacterium, virus, or parasite. In certain embodiments of the invention the subject receives, in addition to a composition of this invention, any agent known in the art to be useful for treating or preventing an infection from which the subject is at risk from which the subject suffers. Thus in one embodiment the method comprises administering to a subject (i) a composition of this invention comprising β1-6 glucan; and (ii) a known anti-fungal, anti-bacterial, anti-viral, or anti-parasitic agent. The composition and anti-fungal agent could be administered in a single composition or separately. In some embodiments, such separate administration may be within up to 24 or up to 48 hours apart, and in some embodiments, less than an hour apart. The composition could be suitable for use in humans, for veterinary applications, or both.

In some embodiments, the use of βglucan and optionally an agent, which biases antibody production to yield relatively greater amounts of immuno globulin G (IgG) 1, 2 or 3 versus immuno globulin G (IgG) 4 thereof of this invention stimulate, enhance or facilitate complement fixation. In some embodiments, this effect is antibody-mediated.

According to this aspect, and in some embodiments, the use of βglucan and optionally an agent, which biases antibody production to yield relatively greater amounts of immunoglobulin G (IgG) 1, 2 or 3 versus immunoglobulin G (IgG) 4 thereof of this invention stimulates, enhances or promotes immune responses, which involve complement fixation, resulting in therapeutic effects in the subject. In some embodiments, such use may be directed to treating sepsis in the subject. In some embodiments, such use may be directed to treating Chagas disease in a subject, a pulmonary pathogen, or a parasite or helminth. In some embodiments, such use is directed to treating a viral infection, such as HSV.

In some embodiments, the methods according to this aspect of the invention may further comprise administration of an agent which promotes elaboration of the complement cascade. In some embodiments, according to this aspect of the invention, the methods may further comprise administration of an antibody which specifically recognizes the pathogenic agent with which the subject is infected.

In another embodiment, the method of stimulating an immune response of this invention is directed to stimulating an anticancer response. In one embodiment, the method further comprises exposing the subject to an antigen, which is a tumor-associated antigen. In one embodiment, the subject has a hyperplastic or preneoplastic lesion. In another embodiment, the subject has cancer.

In one embodiment, cancers associated with the following cancer antigen may be treated or prevented by the methods and compositions of the invention. KS ¼ pan-carcinoma antigen (Perez and Walker, 1990, J. Immunol. 142:32-37; Bumal, 1988, Hybridoma 7(4):407-415), ovarian carcinoma antigen (CA125) (Yu et al., 1991, Cancer Res. 51(2):48-475), prostatic acid phosphate (Tailor et al., 1990, Nucl. Acids Res. 18(1):4928), prostate specific antigen (Henttu and Vihko, 1989, Biochem. Biophys. Res. Comm. 10(2):903-910; Israeli et al., 1993, Cancer Res. 53:227-230), melanoma-associated antigen p97 (Estin et al., 1989, J. Natl. Cancer Instit. 81 (6):445-44), melanoma antigen gp75 (Vijayasardahl et al., 1990, J. Exp. Med. 171(4):1375-1380), high molecular weight melanoma antigen (HMW-MAA) (Natali et al., 1987, Cancer 59:55-3; Mittelman et al., 1990, J. Clin. Invest. 86:2136-2144)), prostate specific membrane antigen, carcinoembryonic antigen (CEA) (Foon et al., 1994, Proc. Am. Soc. Clin. Oncol. 13:294), polymorphic epithelial mucin antigen, human milk fat globule antigen, Colorectal tumor-associated antigens such as: CEA, TAG-72 (Yokata et al., 1992, Cancer Res. 52:3402-3408), CO17-1A (Ragnhammar et al., 1993, Int. J. Cancer 53:751-758); GICA 19-9 (Herlyn et al., 1982, J. Clin. Immunol. 2:135), CTA-1 and LEA, Burkitt's lymphoma antigen-38.13, CD19 (Ghetie et al., 1994, Blood 83:1329-1336), human B-lymphoma antigen-CD20 (Reffet al., 1994, Blood 83:435-445), CD33 (Sgouros et al., 1993, J. Nucl. Med. 34:422-430), melanoma specific antigens such as ganglioside GD2 (Saleh et al., 1993, J. Immunol., 151, 3390-3398), ganglioside GD3 (Shitara et al., 1993, Cancer Immunol. Immunother. 36:373-380), ganglioside GM2 (Livingston et al., 1994, J. Clin. Oncol. 12:1036-1044), ganglioside GM3 (Hoon et al., 1993, Cancer Res. 53:5244-5250), tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellstrom et al., 1985, Cancer. Res. 45:2210-2188), differentiation antigen such as human lung carcinoma antigen L6, L20 (Hellstrom et al., 1986, Cancer Res. 46:3917-3923), antigens of fibrosarcoma, human leukemia T cell antigen-Gp37 (Bhattacharya-Chatterjee et al., 1988, J. of Immun. 141:1398-1403), neoglycoprotein, sphingolipids, breast cancer antigen such as EGFR (Epidermal growth factor receptor), HER2 antigen (p185HER2), polymorphic epithelial mucin (PEM) (Hilkens et al., 1992, Trends in Bio. Chem. Sci. 17:359), malignant human lymphocyte antigen-APO-1 (Bernhard et al., 1989, Science 245: 301-304), differentiation antigen (Feizi, 1985, Nature 314: 53-57) such as I antigen found in fetal erythrocytes and primary endoderm, I(Ma) found in gastric adenocarcinomas, M18 and M39 found in breast epithelium, SSEA-1 found in myeloid cells, VEP8, VEP9, Myl, VIM-D5, and D156-22 found in colorectal cancer, TRA-1-85 (blood group H), C14 found in colonic adenocarcinoma, F3 found in lung adenocarcinoma, AH6 found in gastric cancer, Y hapten, Ley found in embryonal carcinoma cells, TL5 (blood group A), EGF receptor found in A431 cells, E1 series (blood group B) found in pancreatic cancer, FC10.2 found in embryonal carcinoma cells, gastric adenocarcinoma, CO-514 (blood group Lea) found in adenocarcinoma, NS-10 found in adenocarcinomas, CO-43 (blood group Leb), G49, EGF receptor, (blood group ALeb/Ley) found in colonic adenocarcinoma, 19.9 found in colon cancer, gastric cancer mucins, T5A7 found in myeloid cells, R24 found in melanoma, 4.2, GD3, D1.1, OFA-1, GM2, OFA-2, GD2, M1:22:25:8 found in embryonal carcinoma cells and SSEA-3, SSEA-4 found in 4-8-cell stage embryos. In another embodiment, the antigen is a T cell receptor derived peptide from a cutaneous T cell lymphoma (see Edelson, 1998, The Cancer Journal 4:62).

In another embodiment, the antigen is derived from HER2/neu or chorio-embryonic antigen (CEA) for suppression/inhibition of cancers of the breast, ovary, pancreas, colon, prostate, and lung, which express these antigens. Similarly, mucin-type antigens such as MUC-1 can be used against various carcinomas; the MAGE, BAGE, and Mart-1 antigens can be used against melanomas. In one embodiment, the methods may be tailored to a specific cancer patient, such that the choice of antigenic peptide or protein is based on which antigen(s) are expressed in the patient's cancer cells, which may be predetermined by, in other embodiments, surgical biopsy or blood cell sample followed by immunohistochemistry.

In another embodiment, this invention provides for the combined use of β-glucans and an agent, which biases antibody production to yield relatively greater amounts of immunoglobulin G (IgG) 1, 2 or 3 versus immunoglobulin G (IgG) 4 and optionally additional immunomodulatory compounds.

Examples of useful agents include cytokines, chemokines, complement components, immune system accessory and adhesion molecules and their receptors of human or non-human animal specificity. Useful examples include, but are not limited to: GM-CSF, IL-2, IL-12, OX40, OX40L (gp34), lymphotactin, CD40, and CD40L. Further useful examples include, but are not limited to: interleukins for example interleukins 1 to 15, interferons alpha, beta or gamma, tumor necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, TRAP, ICAM-1, 2 or 3 and cytokine receptors. OX40 and OX40-ligand (gp34) are further useful examples of immuno-modulatory proteins. It is to be understood that any agent, which stimulates the immune response to and in the process participates in the biasing, or facilitates the activation of the biased response, in concert with the glucans as herein described in a given immune response may be used in accordance with the methods of this invention, and is to be considered an embodiment thereof.

In one embodiment, uses according to this invention, may also comprise administering an additional therapeutic, which may comprise an anti-inflammatory agent such as betamethasone, prednisolone, piroxicam, aspirin, flurbiprofen and (+)-N-{4-[3-(4-fluorophenoxy)phenoxy]-2-cyclopenten-1-yl}-N-hyroxyurea; an antiviral such as acyclovir, nelfinavir, or virazole; an antibiotic such as ampicillin and penicillin G or belonging to the family of penicillines, cephalosporins, aminoglycosidics, macrolides, carbapenem and penem, beta-lactam monocyclic, inhibitors of beta-lactamases, tetracyclins, polipeptidic antibiotics, chloramphenicol and derivatives, fusidic acid, lincomicyn, novobiocine, spectinomycin, polyetheric ionophores, quinolones; an anti-infective such as benzalkonium chloride or chlorhexidine; dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; an antiinflammatory such as diflunisal, ibuprofen, indomethacin, meclofenamate, mefenamic acid, naproxen, oxyphenbutazone, phenylbutazone, piroxicam, sulindac, tolmetin, aspirin and salicylates; antifungal such as amphotericin B, glucan synthesis inhibitors such as caspofungin, micafungin, or anidulafungin (LY303366), econazole, terconazole, fluconazole, voriconazole or griseofulvin; an antiprotozoal such as metronidazole; an imidazole-type anti-neoplastic such as tubulazole; an anthelmintic agent such as thiabendazole or oxfendazole; an antihistamine such as astemizole, levocabastine, cetirizine, or cinnarizine; a decongestant such as pseudoephedrine; antipsychotics such as fluspirilene, penfluridole, risperidone or ziprasidone; an antineoplastic agent such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea, procarbazine, and dacarbazine; a mitotic inhibitor such as etoposide, colchicine, and the vinca alkaloids, a radiopharmaceutical such as radioactive iodine and phosphorus product, or any combination thereof.

In some embodiments, the methods of this invention are used to therapeutically or prophylactically treat animals or humans who are at a heightened risk of infection due to imminent surgery, injury, illness, radiation or chemotherapy, or other condition which deleteriously affects the immune system. In some embodiments, the methods of this invention are used to treat patients who have a disease or disorder which causes the normal immune response to be reduced or depressed, such as HIV infection (AIDS) or who are receiving immunosuppressive therapy (e.g., individuals who are transplant candidates or have received a transplant, individuals suffering from an autoimmune disease, etc.). In some embodiments, the methods of this invention are used to pre-initiate an immune response in patients who are undergoing chemotherapy or radiation therapy, or who are at a heightened risk for developing secondary infections or post-operative complications because of a disease, disorder or treatment resulting in a reduced ability to mobilize the body's normal responses to infection.

In one embodiment, stimulating said immune response comprises stimulating an antigen-specific response In some embodiments, use of the glucans as described herein, and methods as herein described may function to enhance complement-mediated lysis in a subject. In some embodiments, such enhancement may involve the phagocytic cell response, for example, enhancing neutrophil or macrophage, or other professional antigen presenting cell phagocytosis and cytotoxic responses. In some embodiments, such enhancement may be independent of phagocytic cell involvement, for example, by enhancing membrane attack complex formation and/or activity.

It is to be understood that the methods of this invention which by stimulating an immune response, in turn prevent disease, and/or ameliorate disease, and/or alter disease progression are to be considered as part of this invention.

In some embodiments, the term "contacting" or "administering" refers to both direct and indirect exposure to the indicated material.

In some embodiments, the methods of this invention make use of a non-sterile or sterile carrier or carriers for administration of the described agents to cells, tissues or organisms, such as a pharmaceutical carrier suitable for administration to an individual. Such carriers may include, but are not limited to, saline, buffered saline, dextrose, water, glycerol, and combinations thereof. The formulation should suit the mode of administration.

The agents may be administered in any effective, convenient manner including, for instance, administration by intravascular (i.v.), intramuscular (i.m.), intranasal (i.n.), subcutaneous (s.c.), oral, rectal, intravaginal delivery, or by any means in which the glucan/composition can be delivered to tissue (e.g., needle or catheter). Alternatively, topical administration may be desired for insertion into epithelial cells. Another method of administration is via aspiration or aerosol formulation. In some embodiments the methods comprise administration of the described agents/glucans by implanting or introducing into the body of a subject, an implant or other medical or surgical device that comprises the glucan, e.g., as a component of a coating layer.

In one embodiment, the invention provides a food supplement comprising β1-6 glucan and/or other agents described herein.

In some embodiments, a food or food product is any substance that is substantially non-toxic that can be metabolized by an organism to give energy and build tissue. In some embodiments, a food or food product denotes a product intended for ingestion by a mammal, e.g., by humans, which has nutritional value. In some embodiments a food or food product denotes a product regulated as a food or food product by the U.S. Food and Drug Administration (FDA). In some embodiments, a food or food product is a product packaged in a container bearing a label indicating that the product is a food or food product. In some embodiments, a food or food product is a product packaged in a container bearing a label providing nutritional information regarding the product, such as the calorie, fat, or protein content, or the content of one or more vitamins or minerals. In some embodiments a food supplement (also referred to as a "dietary supplement") is any substance that is added to a food or food product. In some embodiments the food supplement comprises, in addition to a glucan of this invention, one or more essential nutrients, such as vitamins, minerals, and protein. In some embodiments, the food supplement is any product intended for ingestion as a supplement to the diet and may comprise, in addition to a glucan of this invention, one or more vitamins, minerals, herbs, botanicals, and other plant-derived substances; amino acids; and concentrates, metabolites, constituents and extracts of these substances. In some embodiments, the food, food product, food supplement, or cosmetic composition is not intended to diagnose, cure, mitigate, treat, or prevent disease. In some embodiments, the food supplement is provided in a container or other packaging material labeled to indicate that the contents are a food or dietary supplement, e.g., in accordance with then current U.S. law and/or FDA guidelines. In some embodiments, the food supplement or product comprises about 0.01 to 30 w/w % of the glucan, and may additionally comprise vitamins, oligosaccharides, dietary ingredients, proteins, or a combination thereof.

In some embodiments, the ratio of the components is not fixed, or in other embodiments, such ratio may range from about 0.01 to 30 w/w % per 100 w/w %. Examples of food comprising aforementioned glucan of this invention therein are various food, beverage, gum, vitamin complex, health improving food and the like.

The composition may additionally comprise one or more than one of organic acid, such as citric acid, fumaric acid, adipic acid, lactic acid, malic acid; phosphate, such as phosphate, sodium phosphate, potassium phosphate, acid pyrophosphate, polyphosphate; natural anti-oxidants, such as polyphenol, catechin, alpha-tocopherol, rosemary extract, vitamin C, licorice root extract, chitosan, tannic acid, phytic acid etc.

In some embodiments, the agents/glucans administered as part of the methods of this invention are formulated as a topical ointment, lotion, gel, or cream containing the active ingredient(s) in an amount of, for example, 0.0001 to 50% w/w, e.g., 0.075 to 20% w/w (including active ingredient(s) in a range between 0.1% and 20% in increments of 0.1% w/w such as 0.6% w/w, 0.7% w/w, etc.), often 0.2 to 15% w/w and most often 0.5 to 10% w/w). In some embodiments, when formulated in an ointment, the active ingredients may be employed with either a paraffinic or a water-miscible ointment base. In some embodiments, the active ingredients may be formulated in a cream with an oil-in-water cream base.

In some embodiments, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. In some embodiments, the topical formulations may include a compound that enhances absorption or penetration of the active ingredient(s) through the skin or other affected areas. Examples of such dermal penetration enhancers include dimethyl sulphoxide and related analogs.

In some embodiments, the, the agents/glucans administered as part of the methods of this invention are formulated for use as eye drops wherein the active ingredient(s) is dissolved or suspended in a suitable excipient(s), for example, an aqueous solvent for active ingredient(s) that comprise one or more charges at pH values near neutrality, e.g., about pH 6-8. In some embodiments, the active ingredient(s) is present in such formulations in a concentration of about 0.5-20% w/w, typically about 1-10% w/w, often about 2-5% w/w.

In some embodiments, the agents/glucans administered as part of the methods of this invention are formulated for topical administration in the mouth, and may include lozenges comprising the active ingredient in a flavored basis, which may comprise sucrose and acacia or tragacanth; pastilles comprising the active ingredient(s) in an inert basis such as gelatin and glycerin, or sucrose and acacia, or others; or mouthwashes comprising the active ingredient in a suitable liquid excipient(s), or others as will be appreciated by one skilled in the art.

Formulations for rectal administration may be presented as a suppository with a suitable base comprising for example cocoa butter or a salicylate.

Formulations suitable for intrapulmonary or nasal administration have a particle size for example in the range of 0.01 to 500 microns (including average particle sizes in a range between 0.01 and 500 microns in 0.1 micron or other increments, e.g., 0.05, 0.1, 0.5, 1, 1.5, 2.0, 2.5, 3.0, 3.5, 4.0, 4.5, 5.0, 6, 7, 8, 9, 10, 20, 25, 30, 35, 50, 75, 100, etc. microns), which is administered by rapid inhalation through the nasal passage or by inhalation through the mouth so as to reach the alveolar sacs. Suitable micronized formulations include aqueous or oily solutions or suspensions of the active ingredient(s). Formulations suitable for aerosol, dry powder or tablet administration may be prepared according to conventional methods and may be delivered with other therapeutic agents such as compounds heretofore used in the treatment or prophylaxis of viral or other infections as described herein. Such formulation may be administered, e.g., orally, parenterally (i.v., i.m., s.c.), topically or by a buccal route.

Formulations suitable for vaginal administration may be presented as pessaries, tampons, creams, gels, pastes, foams or spray formulations containing in addition to the active ingredient(s) such excipients as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampules and vials, and may be stored in a freeze-dried (lyophilized) condition requiring only the addition of the sterile liquid excipient, for example water for injection, immediately prior to use. Extemporaneous injection solutions and suspensions are prepared from sterile powders, granules and tablets of the kind previously described. Unit dosage formulations are those containing a daily dose or unit daily sub-dose, as recited herein, or an appropriate fraction thereof, of the active ingredient(s).

It should be understood that in addition to the ingredients particularly mentioned above the formulations of this invention may include other agents or excipients conventional in the art having regard to the type of formulation in question, for example those suitable for oral administration may include flavoring agents.

It will be apparent to those skilled in the art that various modifications and variations can be made in the compositions, use and preparations of the present invention without departing from the spirit or scope of the invention.

For administration to mammals, and particularly humans, it is expected that in the case of medications, the physician or other qualified health care provider may determine the actual dosage and duration of treatment, which will be most suitable for an individual and can vary with the age, weight and response of the particular individual. It will be appreciated that in the case of non-prescription (e.g., "over-the-counter") medications, foods, food products, food supplements, cosmetic and personal care compositions, the amount may be determined at the discretion of the user, optionally with guidance from the labeling or from an appropriate health care provider or other advisor.

EXAMPLES

Materials and Methods

Preparation of IgG-Depleted Serum

Protein G-sepharose beads of untreated sepharose beads (control) were washed three times with PBS. Serum was diluted 2-fold in PBS and added to beads. Beads were incubated at room temperature on an end-to-end mixer for 30 min. beads were removed by centrifugation.

Serum from 10 unimmunized normal healthy donors was pooled

SRBC Assay

SRBC (Accurate chemical and scientific corp.) were washed with gelatin veronal buffer (Sigma) and opsonized with rabbit anti-SRBC antibodies (Accurate chemical and scientific corp.) for 30 minutes at room temperature. IgG-depleted serum (from protein G-sepharose beads) or IgG-containing serum (from untreated sepharose beads) were added to SRBC and incubated at 37° C. for one hour. Water was added as a positive control (complete lysis), and buffer was added as a negative control (no lysis). Lysis was detected by direct microscopic visualization (FIG. 1C a) or by O.D. 414 nm, which detects the heme that is secreted from the lysing SRBC).

Preparation of β-1,6-Glucan-Coated Beads and FACS Analysis (Phagocytosis and ROS Production)

These methods were performed as described in. Rubin-Bejerano, I., et al., Phagocytosis by human neutrophils is stimulated by a unique fungal cell wall component. Cell Host Microbe, 2007. 2(1): p. 55-67.

Cell Culture

SK-BR-3 cells (ATCC) were cultured in McCoy's 5A Medium (Gibco) supplemented with 10% FBS.

Conjugation

Herceptin (Genentech, Inc.) or IgG1 isotype control (Sigma) were conjugated to β-1,6-glucan following oxidation with sodium meta periodate (Pierce).

Neutrophils

Fresh human blood and serum were provided by Research Blood Components (Brighton, Mass.). Neutrophils were isolated from fresh human blood in accordance with a protocol approved by the MIT Committee on Use of Humans as Experimental Subjects by using Histopaque 1077 and Histopaque 1119 (Sigma).

Opsonization

Breast cancer cells were opsonized in 40% serum in Phosphate-Buffered Saline without calcium chloride and without magnesium chloride (PBS) (Gibco) for 15 minutes at 37° C. Cells were then washed three times with cold PBS supplemented with 0.04 mg/ml of the protease inhibitor AEBSF (Sigma).

Antibody Binding and C3 Deposition

Fluorescence Activated Cell Sorting (FACS) analysis was used to detect Herceptin binding to breast cancer cells (by using anti-human IgG1 antibodies, Sigma) and C3 deposition (by using anti-human C3 antibodies, Accurate Chem.).

Cytotoxicity

Cytotoxicity to breast cancer cells following incubation with β-1,6-glucan-conjugated or unconjugated Herceptin and serum was determined by CytoTox 96® Non-Radioactive Cytotoxicity Assay (Promega), which detects lactate dehydrogenase released from lysed cells. For neutrophil-dependent killing, above cells were cultured with neutrophils at 37° C. after which cytotoxicity was measured.

Example 1

β-1,6-Glucan Stimulated Complement Activation is Dependent Upon Antibodies

In order to test whether antibodies are involved in complement activation by β-1,6-glucan, serum used in complement activation assays was depleted of antibodies by using protein G sepharose beads. This IgG-depleted serum was used to opsonize β-1,6-glucan-coated beads. The beads were then tested in a phagocytosis assay conducted with human neutrophils Phagocytosis and ROS production were reduced when β-1,6-glucan-coated beads were opsonized with IgG-depleted serum (FIGS. 1A and B), suggesting that the Classical pathway plays a major role in complement activation by β-1,6-glucan.

The IgG-depleted serum contained functional complement factors. In a sheep red blood cells (SRBC) assay, SRBC opsonized with anti-SRBC antibody were lysed when IgG-depleted serum was utilized (FIG. 1 C).

Example 2

Antibodies to β-1,6-Glucan are Prevalent in Normal Adults

Figure 2:
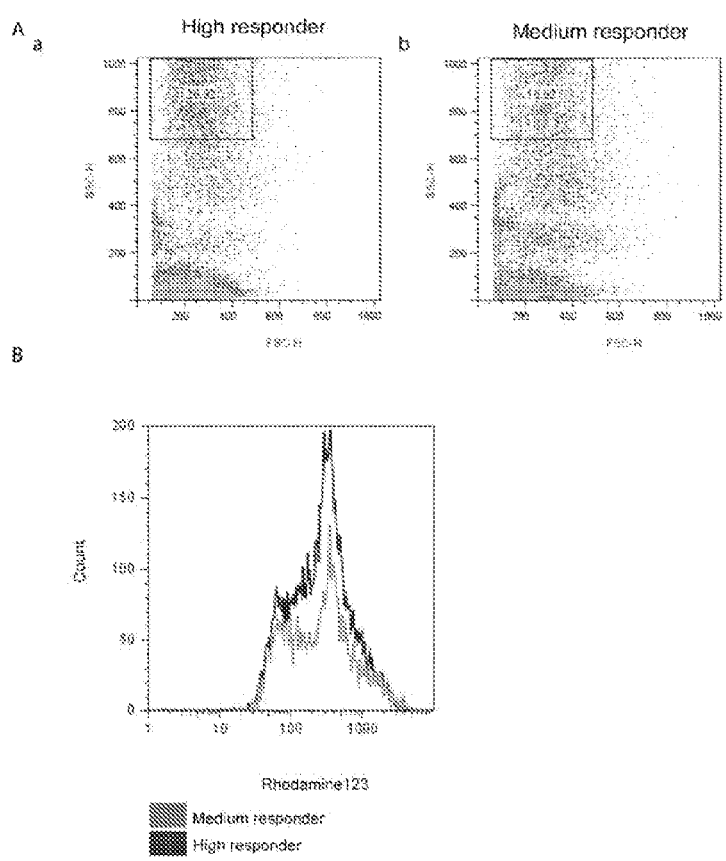
FIG. 2 demonstrates that β-1,6-glucan antibodies are prevalent in normal adult sera.

Pooled serum from 10 human donors, had high levels of IgG antibodies binding β-1,6-glucan, in contrast to low levels of IgG binding β-1,3-glucan. To test how prevalent is the anti-β-1,6-glucan antibodies in different donors, we collected sera from 12 individuals. The sera were used to opsonize β-1,6-glucan- or β-1,3-glucan-coated beads, and the beads were incubated with human neutrophils. Eleven of the twelve sera had the high response that the pool did, mediating efficient engulfment and ROS production (FIG. 2 Aa, a representative serum of the high responders). One serum mediated a less efficient engulfment and ROS production (FIG. 2 Ab, low responder).

Figure 3:
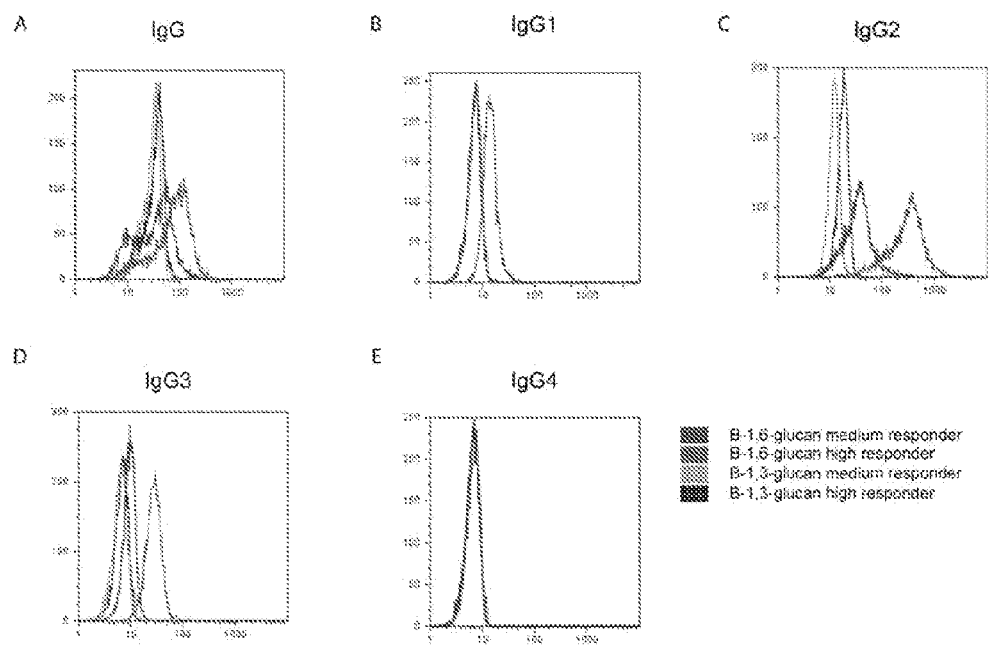
FIG. 3 demonstrates that select IgG isotypes influence responsiveness to β-glucan.

Example 3

β-1,6-Glucan Mediates Efficient Phagocytosis and Production of Reactive Oxygen Species by Neutrophils In order to assess which isotype of IgG was mediating the β-1,6-glucan recognition, antibodies specific for IgG1, IgG2, IgG3, or IgG4 were used to determine the IgG isotype usage in donor serum with a high or low response to β-1,6-glucan, following exposure to opsonized β-1,6-glucan-coated beads. The high responder produced more IgG1, IgG2, and IgG3, but not IgG4, as compared to the low responder (FIG. 3). Specifically, the level of IgG2 was dramatically higher in the high responder, probably because polysaccharides tend to induce production of the IgG2 isotype.

The different isotypes differ in their complement activation properties. IgG3 has the highest complement activation properties, then follows IgG1, IgG2 is next, and IgG4 cannot activate complement. IgG2 is a poor activator of the Classical pathway, but it can activate complement through the alternative pathway, and is a good substrate for phagocytosis by neutrophils.

Example 4

β-1,6-Glucan Conjugated to the Herceptin Monoclonal Antibody Mediates Recruitment of Complement and Neutrophils to Breast Cancer Cells

Figure 4:
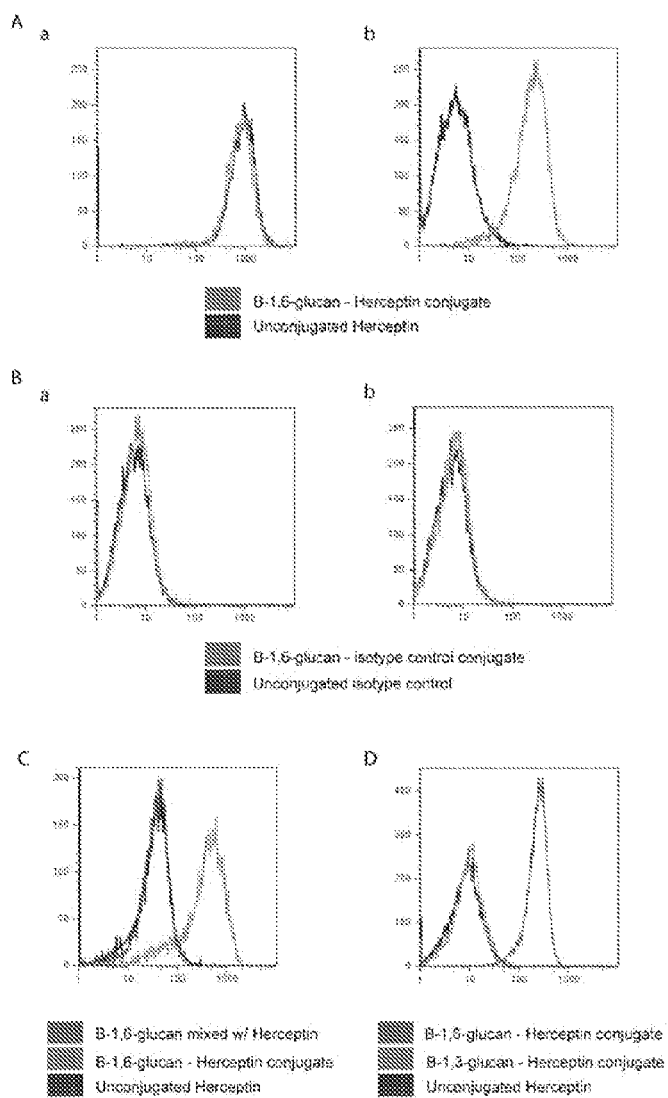
FIG. 4 demonstrates that a β-1,6-glucan-Herceptin conjugate is functional.

In order to assess whether conjugated β-1,6-glucan linked to targeting moieties can mediate recruitment of complement and neutrophils to lyse and kill target cells bound by the targeting moieties, a 1,6-glucan linked to a Herceptin monoclonal antibody (mAb) was tested in a system of breast cancer cells (SK-BR-3). The Herceptin mAb is directed against the Her-2/neu protein overexpressed on SK-BR-3 cells. Conjugation of β-1,6-glucan to Herceptin did not affect its binding to breast cancer cells (FIG. 4 Aa). Furthermore, the conjugate mediated high C3 deposition (FIG. 4 Ab), suggesting that β-1,6-glucan remained functional. Non-specific isotype control antibodies conjugated to β-1,6-glucan did not bind breast cancer cells (FIG. 4 Ba), and therefore, did not mediate complement activation and C3 deposition on these cells (FIG. 4 Bb). Mixing β-1,6-glucan with the mAb without chemical conjugation did not mediate C3 deposition on these breast cancer cells (FIG. 4 C, compare green to blue). Therefore, it was concluded that the conjugation of β-1,6-glucan to the targeting moiety was required for directing of complement and consequently neutrophils to target cells. C3 deposition was detected on breast cancer cells treated with Herceptin conjugated to β-1,6-glucan but not β-1,3-glucan (FIG. 4 D, compare blue to green), suggesting that indeed β-1,6-glucan was more efficient than β-1,3-glucan in attracting complement.

Example 4

β-1,6-Glucan Conjugated to the Herceptin Monoclonal Antibody Mediates Killing of Breast Cancer Cells by Complement and Neutrophils

Figure 5:
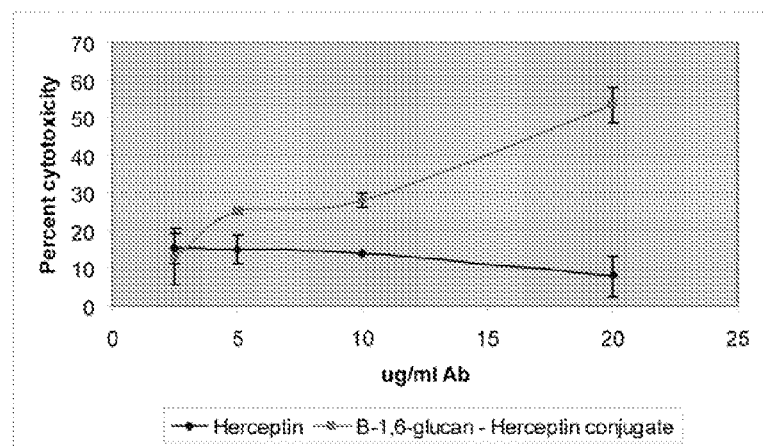
FIG. 5 demonstrates that a β-1,6-glucan-Herceptin conjugate mediates the killing of cancer cells by complement and neutrophils.
Figure 5:
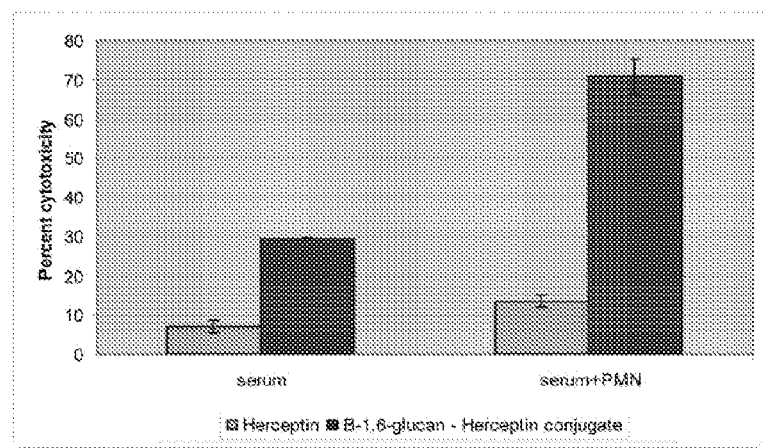

Deposition of the complement protein C3 on breast cancer cells led to lysis of these cancer cells. The Herceptin-β-1,6-glucan conjugate showed a dose-dependent cytotoxic effect on the breast cancer cells, whereas the unconjugated Herceptin lacked any effect (FIG. 5 A). Furthermore, the Herceptin-β-1,6-glucan conjugate showed an increased neutrophil killing of the cancer cells (FIG. 5 B).

EQUIVALENTS AND SCOPE

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g., in Markush group format or the like, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A method comprising steps of:
   assessing relative immunoglobulin G (IgG) isotype titers to β-1,6-glucan in a subject;
   correlating the presence of a higher titer of IgG1 or IgG2 or IgG3, or a combination thereof, compared to IgG4 with responsiveness to a vaccine, adjuvant or composition comprising β-1,6-glucan; and
   administering the vaccine, adjuvant or composition comprising β-1,6-glucan to the subject based on the presence of a higher titer of IgG1 or IgG2 or IgG3, or a combination thereof, versus IgG4.

2. The method of claim 1, wherein the step of correlating comprises correlating the presence of a higher titer of IgG2 versus IgG4 with responsiveness to the vaccine, adjuvant or composition comprising β-1,6-glucan; and
   wherein the step of administering comprises administering the vaccine, adjuvant or composition comprising β-1,6-glucan to the subject based on the presence of a higher titer of IgG2 versus IgG4.

3. The method of claim 1, wherein the step of assessing is practiced on a biological sample isolated from the subject.

4. The method of claim 3, wherein the biological sample is serum or plasma.

5. The method of claim 1, wherein the relative immunoglobulin G (IgG) isotype titers are assessed using anti-IgG subclass-specific antibodies.

6. The method of claim 5, wherein the anti-IgG subclass-specific antibodies are labeled with a detectable marker.

7. The method of claim 6, wherein the detectable marker is selected from the group consisting of radioactive labels, fluorescent labels, chemiluminescent labels, chromophoric labels, ligands, fluorescein, radioisotopes, phosphatase, biotin, biotin-related compounds, avidin, avidin-related compounds, and peroxidase.

8. The method of claim 1, wherein the vaccine, adjuvant or composition comprises β-1,6-glucan linked to an antibody.

9. The method of claim 8, wherein the antibody is a monoclonal antibody.

10. The method of claim 8, wherein the antibody is a human antibody.

11. The method of claim 8, wherein the antibody is a humanized antibody.

12. The method of claim 8, wherein the antibody is an antibody fragment.

13. The method of claim 12, wherein the antibody fragment is a Fab fragment, Fab' fragment, (Fab')$_2$ fragment, Fv fragment, a single chain antibody or a peptide coding for a single complementarity-determining region.

14. The method of claim 8, wherein the antibody is selected from the group consisting of Alemtuzumab, Bevacizumab, Cetuximab, Gemtuzumab, Ibritumomab, Panitumumab, Rituximab, Tositumomab, Trastuzumab and Palivizumab.

15. The method of claim 8, wherein the antibody targets a neoplastic or preneoplastic cell.

16. The method of claim 15, wherein the vaccine, adjuvant or composition comprising β-1,6-glucan promotes a host anticancer response.

17. The method of claim 15, wherein the vaccine, adjuvant or composition comprising β-1,6-glucan promotes tumor cell lysis.

18. The method of claim 15, wherein the vaccine, adjuvant or composition comprising β-1,6-glucan enhances a host antitumor response.

19. The method of claim 8, wherein the antibody targets an antigen expressed specifically on cancer cells.

20. The method of claim 19, wherein the vaccine, adjuvant or composition comprising β-1,6-glucan enhances complement-mediated lysis of the cancer cells.

21. The method of claim 1 further comprising administering an agent to the subject which biases antibody production to yield relatively greater amounts of IgG1 or IgG2 or IgG3, or a combination thereof, versus IgG4; wherein the agent is administered prior to the vaccine, adjuvant or composition comprising β-1,6-glucan.

22. The method of claim 21, wherein the agent is selected from the group consisting of cytokines, chemokines, complement components, immune system accessory and adhesion molecules and receptors of any of these.

23. The method of claim 22, wherein the agent is selected from the group consisting of interleukin 2, interleukin 12, interferon-gamma and combinations thereof.

24. The method of claim 21, wherein the agent is administered based on the presence of a lower titer of IgG1 or IgG2 or IgG3, or a combination thereof, versus IgG4.

25. The method of claim 21, wherein the agent is administered based on the presence of a lower titer of IgG2 versus IgG4.

26. The method of claim 2, wherein the composition is a pharmaceutical composition.

27. The method of claim 1, wherein the immunoglobulin G (IgG) isotype titers to β-1,6-glucan result from exposure to environmental β-1,6-glucan.

28. The method of claim 1, wherein the method comprises:
    assessing relative IgG2 and IgG4 isotype titers to β-1,6-glucan in the subject;
    correlating the presence of a higher titer of IgG2 versus IgG4 with responsiveness to a vaccine, adjuvant or composition comprising β-1,6-glucan; and
    administering the vaccine, adjuvant or composition comprising β-1,6-glucan to the subject based on the presence of a higher titer IgG2 versus IgG4.

29. The method of claim 28, wherein the vaccine, adjuvant or composition comprises β-1,6-glucan linked to an antibody.

30. A method comprising steps of:
    assessing a level of immunoglobulin G (IgG) 2 isotype titers to β-1,6-glucan in a subject;
    correlating a level of IgG2 above a threshold with responsiveness to a vaccine, adjuvant or composition that comprises β-1,6-glucan; and
    administering the vaccine, adjuvant or composition that comprises β-1,6-glucan to the subject based on the presence of a level of IgG2 above the threshold.

31. The method of claim 30, wherein the glucan based vaccine, adjuvant or composition comprises β-1,6-glucan linked to an antibody.

32. The method of claim 31, wherein the composition is a pharmaceutical composition.

33. The method of claim 1, wherein the vaccine, adjuvant or composition comprises β-1,6-glucan linked to an aptamer.

34. The method of claim 1, wherein the vaccine, adjuvant or composition comprises β-1,6-glucan linked to a peptide.

35. The method of claim 28, wherein the vaccine, adjuvant or composition comprises β-1,6-glucan linked to an aptamer.

36. The method of claim 28, wherein the vaccine, adjuvant or composition comprises β-1,6-glucan linked to a peptide.

37. The method of claim 30, wherein the vaccine, adjuvant or composition comprises β-1,6-glucan linked to an aptamer.

38. The method of claim 30, wherein the vaccine, adjuvant or composition comprises β-1,6-glucan linked to a peptide.

* * * * *

UNITED STATES PATENT AND TRADEMARK OFFICE
CERTIFICATE OF CORRECTION

PATENT NO.         : 8,617,823 B2  
APPLICATION NO.    : 12/990066  
DATED              : December 31, 2013  
INVENTOR(S)        : Ifat Rubin-Bejerano et al.

Page 1 of 1

It is certified that error appears in the above-identified patent and that said Letters Patent is hereby corrected as shown below:

In the Claims:

Column 44, line 29, correct claim 31 from:

"The method of claim 30, wherein the glucan based vaccine, adjuvant or composition comprises β-1,6-glucan linked to an antibody."

to read:

-- The method of claim 30, wherein the vaccine, adjuvant or composition comprises β-1,6-glucan linked to an antibody. --

Signed and Sealed this  
First Day of April, 2014

Michelle K. Lee  
*Deputy Director of the United States Patent and Trademark Office*

UNITED STATES PATENT AND TRADEMARK OFFICE
CERTIFICATE OF CORRECTION

PATENT NO.        : 8,617,823 B2                                        Page 1 of 1
APPLICATION NO.   : 12/990066
DATED             : December 31, 2013
INVENTOR(S)       : Rubin-Bejerano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 304 days.

Signed and Sealed this
Twenty-second Day of September, 2015

Michelle K. Lee
*Director of the United States Patent and Trademark Office*